(12) United States Patent
Sutherland et al.

(10) Patent No.: US 10,787,514 B2
(45) Date of Patent: *Sep. 29, 2020

(54) CD33 ANTIBODIES AND USE OF SAME TO TREAT CANCER

(71) Applicant: SEATTLE GENETICS, INC., Bothell, WA (US)

(72) Inventors: May Kung Sutherland, Bothell, WA (US); Maureen Ryan, Bothell, WA (US); Django Sussman, Bothell, WA (US); Patrick Burke, Bothell, WA (US); Scott Jeffrey, Bothell, WA (US)

(73) Assignee: SEATTLE GENETICS, INC., Bothell, WA (US)

( * ) Notice: Subject to any disclaimer, the term of this patent is extended or adjusted under 35 U.S.C. 154(b) by 221 days.

This patent is subject to a terminal disclaimer.

(21) Appl. No.: 15/411,947

(22) Filed: Jan. 20, 2017

(65) Prior Publication Data

US 2017/0204180 A1    Jul. 20, 2017

Related U.S. Application Data

(63) Continuation of application No. 14/401,837, filed as application No. PCT/US2013/041209 on May 15, 2013, now Pat. No. 9,587,019.

(60) Provisional application No. 61/649,110, filed on May 18, 2012.

(51) Int. Cl.
| | | |
|---|---|---|
| C07K 16/28 | (2006.01) | |
| A61K 39/00 | (2006.01) | |
| A61K 31/551 | (2006.01) | |
| A61K 47/68 | (2017.01) | |

(52) U.S. Cl.
CPC ........ *C07K 16/2803* (2013.01); *A61K 31/551* (2013.01); *A61K 47/6851* (2017.08); *C07K 16/2896* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/567* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,419,811 | B2 | 9/2008 | Lavie et al. |
| 8,455,622 | B2 | 6/2013 | McDonagh et al. |
| 9,061,074 | B2 | 6/2015 | Carter et al. |
| 9,587,019 | B2 | 3/2017 | Sutherland et al. |
| 2002/0022031 | A1 | 2/2002 | Goldenberg et al. |
| 2007/0190060 | A1 | 8/2007 | Boghaert et al. |
| 2008/0104734 | A1 | 5/2008 | Kav et al. |
| 2010/0158909 | A1 | 6/2010 | McDonagh et al. |
| 2011/0206700 | A1 | 8/2011 | Hoffee et al. |
| 2011/0300139 | A1 | 12/2011 | Kumar et al. |
| 2012/0082670 | A1 | 4/2012 | Konopitzky et al. |
| 2012/0251554 | A1 | 10/2012 | Bachmann et al. |
| 2013/0028919 | A1 | 1/2013 | Howard et al. |
| 2013/0309223 | A1 | 11/2013 | Sutherland et al. |
| 2014/0086942 | A1 | 3/2014 | Carter et al. |

FOREIGN PATENT DOCUMENTS

| | | | |
|---|---|---|---|
| CA | | 2733223 A1 | 10/2011 |
| WO | WO 04/043344 A2 | | 5/2004 |
| WO | WO 11/130613 A1 | | 10/2011 |
| WO | WO 13/173496 A2 | | 11/2013 |
| WO | WO 14/165119 A1 | | 10/2014 |

OTHER PUBLICATIONS

Almagro & Fransson, Frontiers in Bioscience 2008; 13:1619-33.*
De Genst et al., Developmental and Comparative Immunology, 2006, 30:187-98.*
Ward et al., Nature, 1989, 341:544-546.*
Barthelemy et al. (Journal of Biological Chemistry, 2008, 283:3639-3654).*
Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
U.S. Appl. No. 61/649,110, filed May 18, 2012, Expired.
U.S. Appl. No. 13/804,227, filed Mar. 14, 2013, US 2013-0309223, Abandoned.
PCT/US2013/041209, May 15, 2013, WO 2013/173496, Expired.
U.S. Appl. No. 14/401,837, filed Nov. 17, 2014, U.S. Pat. No. 9,587,019, Issued.
Casset et al., "A peptide mimetic of an anti-CD4 monoclonal antibody by rational design," Biochemical and Biophysical Research Communications, 307:198-205, (2003).
Chen et al., "Selection and Analysis of an Optimized Anti-VEGF Antibody: Crystal Structure of an Affinity-matures Fab in Complex with Antigen," J. MoL Biol., 293:865-881, (1999).
Feldman et al., "Phase III Randomized Multicenter Study of a Humanized Anti-CD33 Monoclonal Antibody, Lintuzumab, in Combination With Chemotherapy, Versus Chemotherapy (2005) Alone in Patients With Refractory or First-Relapsed Acute Myeloid Leukemia," Journal of Clin Oncol.
Jeffrey et al., "Development of Pyrrolobenzodiazepine-Based Antibody-Drug Conjugates for Cancer,", AACR Annual Meeting, Abstract No. 4321, 1 page, (2013).

(Continued)

*Primary Examiner* — Julie Wu
(74) *Attorney, Agent, or Firm* — Alston & Bird LLP

(57) ABSTRACT

The invention provides murine, chimeric, and humanized antibodies that specifically hind to CD33. The antibodies are useful for treatment and diagnoses of various cancers as well as detecting CD33.

24 Claims, 2 Drawing Sheets

Specification includes a Sequence Listing.

(56) References Cited

OTHER PUBLICATIONS

Kung Sutherland et al., "SGN-CD33A: a novel C033-targeting antibody-drug conjugate using a pyrrolobenzodiazepine dimer is active in models of drug-resistant AML," Blood, 122:1455-1463, (2013).
Lamminmaki et al., "Protein Structure and Folding: Crystal Structure of a Recombinant Anti-estradiol Fab Fragment in Complex with 17β-Estradiol," J. Biol. Chem., 276:36687-36694, (2001).
MacCallum et al., "Antibody-antigen Interactions: Contact Analysis and Binding Site Topography," J. MoL Biol., 262:732-745, (1996).
Padlan et al., "Structure of an antibody—antigen complex: Crystal structure of the HyHEL-10 Fab—lysozyme complex," Proc. Natl. Acad. Sci USA, 86:5938-5942, (1989).
Pascalis et al., "Grafting of "Abbreviated" Complementarity-Determinig Regions Containing Spccficity-Determining Residues Essential for Ligand Contact to Engineer a Less Immunogenic Humanized Monoclonal Antibody," J Immunol, 169:3076-3084, (2002).
Rudikoff et al., Single amino acid substitution altering antigen-binding specificity Proc. Natl. Acad. Sci. USA, 79:1979, (1982).
Vajdos et al., "Comprehensive Functional Maps of the Antigen-binding Site of an Anti-ErbB2 Antibody Obtained with Shotgun Scanning Mutagenesis," J. Mol. Biol., 320:415-428, (2002).
Wu et al., "Humanization of a Murine Monoclonal Antibody by Simultaneous Optimization of Framework and CDR Residues," J. MoL Biol., 294:151-162, (1999).
EPO Application No. EP 13790467.8, Supplementary European Search Report and European Search Opinion, dated Jun. 16, 2016.
U.S. Appl. No. 14/401,837, Non-Final Office Action dated May 27, 2016.
U.S. Appl. No. 14/401,837, Notice of Allowance dated Oct. 14, 2016.
U.S. Appl. No. 13/804,227, Advisory Action dated Nov. 18, 2015.
U.S. Appl. No. 13/804,227, Fianl Office Action dated Aug. 10, 2015.
U.S. Appl. No. 13/804,227, Non-Final Office Action dated Feb. 18, 2016.
U.S. Appl. No. 13/804,227, Non-Final Office Action dated Feb. 27, 2015.
U.S. Appl. No. 13/804,227, Non-Final Office Action dated Mar. 14, 2016.
U.S. Appl. No. 13/804,227, Restriction Requirement dated Sep. 18, 2014.
U.S. Appl. No. 13/826,007, Non-Final Office Action dated Sep. 11, 2015.
WIPO Application No. PCT/US2013/041209, International Preliminary Report on Patentability dated Apr. 21, 2015.
WIPO Application No. PCT/US2013/041209, International Search report and Written Opinion of the International Searching Authority dated Nov. 25, 2013.
EPO Application No. 1817884.2 (Published as EP3421048), European Search Report and European Search Opinion dated Nov. 23, 2018.
EPO Application No. 13790467.8 (Published as EP2850104), European Search Report and European Search Opinion dated Jun. 14, 2016.
"Seattle Genetics Presents Phase lb Data from Vadastuximab Talirine (SGN-CD33A; 33A) in Combination with Standard of Care in Frontline Acute Myeloid Leukemia at ASH Annual Meeting," Seattle Genetics, Inc., Press Release, 4 pages, (2016). [Author Unknown].

* cited by examiner

FIGURE 1A

```
              10        20        30        40        50
         ....|....|....|....|....|....|....|....|....|....|....
2H12 HA  QVQLVQSGAEVKKPGASVKVSCKASGYTFTNYDINWVRQAPGQGLEWMGWIYPGDGSTKY
2H12 HB  ............................................................
2H12 HC  ............................................................
2H12 HD  ............................................................
2H12 HE  .......................................................I....
2H12 HF  ...................................................N.R......
2H12 HG  ............................................................
2H12 HH  ............................................................
2H12 HI  .......................................................I....
m2H12 H  ....Q...P.LVR..TF..I...............................N.R......I....
CDRs                                    *****          **********

60        70        80        90       100       110
         |....|....|....|....|....|........|....|....|....|....|...
2H12 HA  NEKFKARVTMTTDTSTSTAYMELRSLRSDDTAVYYCARGYEDAMDYWGQGTTVTVSS
2H12 HB  ...........A.............................................
2H12 HC  ..........................................S..............
2H12 HD  ............K.............................................
2H12 HE  ..........................................................
2H12 HF  ..........................................................
2H12 HG  ......KA.L................................................
2H12 HH  ................................S..T.....................
2H12 HI  ......KA.L.A..............................S..............
m2H12 H  ......KA.L.A.K.S....LQ.NN.T.ENS...F..S...............S.....
CDRs     ******                          ********
```

FIGURE 1B

```
              10        20        30        40        50        60
         ....|....|....|....|....|....|....|....|....|....|....|
2H12 LA  DIQMTQSPSSLSASVGDRVTITCKASQDINSYLSWFQQKPGKAPKSLIYRANRLVDGVPS
2H12 LB  ..K.........................................................
2H12 LC  ..................................................T.........
2H12 LD  .............................................................
2H12 LE  .............................................................
2H12 LF  ..............................I.N...........................
2H12 LG  ..............................N..................T..........
m2H12 L  ..K.......MY..L.E..I.N........................S..T..........
CDRs                                   **********       *******

70        80        90       100
         ....|....|....|....|....|....|....|....|...
2H12 LA  RFSGSGSGTDFTLTISSLQPEDFATYYCLQYDEFPLTFGGGTKVEIKR
2H12 LB  ................................................
2H12 LC  ................................................
2H12 LD  ........Q.......................................
2H12 LE  ..........Y......................................
2H12 LF  .................................................
2H12 LG  ........Q.Y.......................................
m2H12 L  ........Q.YS......EY..MGI............A...L.L..
CDRs                                *********
```

CD33 ANTIBODIES AND USE OF SAME TO TREAT CANCER

CROSS-REFERENCE TO RELATED APPLICATIONS

This application is a continuation of U.S. 14/401,837 filed Nov. 17, 2014, which is a national stage of PCT/US2013/041209 filed May 15, 2013, incorporated by reference in its entirety for all purposes, which claims the benefit of U.S. 61/649,110 filed May 18, 2012.

REFERENCE TO A SEQUENCE LISTING

This application includes an electronic sequence listing in a file named 491821_SEQLST.TXT, created on Jan. 20, 2017 and containing 55,823 bytes, which is hereby incorporated by reference.

BACKGROUND

CD33 is a 67 kDa plasma membrane protein that binds to sialic acid and is a member of the sialic acid-binding Ig-related lectin (SIGLEC) family of proteins. CD33 is known to be expressed on myeloid cells. CD33 expression has also been reported on a number of malignant cells. Although CD33 has been targeted for treatment of cancer, e.g., acute myeloid leukemia, no effective CD33-targeted treatments are currently on the market. The present invention solves these and other problems.

SUMMARY OF THE CLAIMED INVENTION

Provided herein are monoclonal antibodies that specifically bind to the human CD33 protein and methods of using those antibodies to treat cancers that express the CD33 protein. The monoclonal antibodies contain complementarity determining regions (CDRs) of SEQ ID NOs:19, 20 and 21 in the heavy chain variable region and CDRs of SEQ ID NOs:22, 23, and 24 in the light chain variable region. In some embodiments, at least one CDR has a conserved amino acid substitution. In some embodiments, any differences in CDRs of the mature heavy chain variable region and mature light variable region from SEQ ID NOS:18 and 8 respectively reside in positions H60-H65. The monoclonal antibodies can be murine antibodies, chimeric antibodies or humanized antibodies. A preferred humanized antibody is the h2H12 antibody, as disclosed herein. In one aspect, the invention is a humanized antibody that includes CDRs of SEQ ID NOs:19, 20 and 21 in the heavy chain variable region and CDRs of SEQ ID NOs:22, 23, and 24 in the light chain variable region and additionally has a mature heavy chain variable region with at least 90% identity to SEQ ID NO:18 and a mature light chain region with at least 90% identity to SEQ ID NO:8. In addition, the following amino acid residues of the heavy chain are maintained: H48 is occupied by I, position H66 is occupied by K, position H67 is occupied by A, position H69 is occupied by L, position H71 is occupied by A, and position H94 is occupied by S; and the following amino acid residues of the light chain are maintained: L22 is occupied by N, position L46 is occupied by T, position L69 is occupied by Q, and position L71 by Y.

In a further embodiment, the humanized antibody that includes CDRs of SEQ ID NOs:19, 20 and 21 in the heavy chain variable region and CDRs of SEQ ID NOs:22, 23, and 24 in the light chain variable region and additionally has a mature heavy chain variable region with at least 95% identity to SEQ ID NO:18 and a mature light chain region with at least 95% identity to SEQ ID NO:8.

In another embodiment, the humanized 2H12 antibody has a mature heavy chain that is fused to a heavy chain constant region and a mature light chain that is fused to a light chain constant region. In a further embodiment, the heavy chain constant region is a mutant form of natural human constant region and has reduced binding to an Fcγ receptor relative to the natural human constant region. In another embodiment, the heavy chain constant region is of IgG1 isotype. Exemplary heavy chain constant region amino acid sequences include SEQ ID NO:27 and SEQ ID NO:29, a heavy chain constant region with serine substituting for cysteine at position 239, (S239C). Exemplary light chain constant region amino acid sequences include SEQ ID NO:25.

In one embodiment, the humanized antibody includes a mature heavy chain variable region having an amino acid sequence of SEQ ID NO:18 and a mature light chain variable region having an amino acid sequence of SEQ ID NO: 8.

In one embodiment, the humanized antibody is conjugated to a cytotoxic or cytostatic agent. In a further embodiment, the humanized antibody is conjugated to a cytotoxic agent. A cytotoxic agent can be, e.g., a DNA minor groove binder. A pyrrolo[1,4]benzodiazepine (PBD) is an example of a cytotoxic agent that is a DNA minor groove binder that can be conjugated to the humanized CD33 antibodies disclosed herein. In one embodiment, the PBD is conjugated to the CD33 antibody via an enzyme cleavable linker. In another embodiment, the cytotoxic agent has the formula

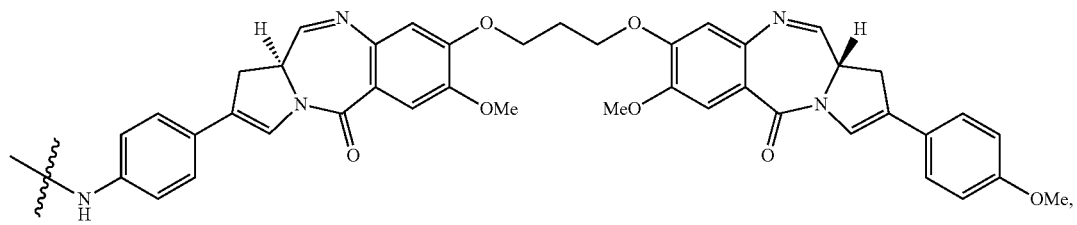 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the site of attachment to the linker.

In one embodiment, the humanized antibody has an association constant for human or cynomolgus monkey CD33 of 0.5 to $2 \times 10^9$ M$^{-1}$.

In one aspect, the invention provides methods of treating a patient having or at risk of having a cancer that expresses CD33, by administering to the patient an effective regime of a humanized antibody CD33 as disclosed herein. The CD33-expressing cancers include acute myeloid leukemia (AML), myelodysplastic syndrome (MDS), acute promyelocytic leukemia (APL), chronic myelogenous leukemia (CML), chronic myelomonocytic leukemia (CMML), a chronic myeloproliferative disorder, precursor B-cell acute lymphoblastic leukemia (preB-ALL), precursor T-cell acute lymphoblastic leukemia (preT-ALL), multiple myeloma (MM), mast cell disease, and myeloid Sarcoma. In one aspect, the invention provides a pharmaceutical composition comprising a humanized or chimeric antibody that contains complementarity determining regions (CDRs) of SEQ ID NOs:19, 20 and 21 in the heavy chain variable region and CDRs of SEQ ID NOs:22, 23, and 24 in the light chain variable region.

In one aspect the invention provides a humanized antibody with a mature heavy chain variable region at least 90% identical to HI, an amino acid sequence of SEQ ID NO:18, and a mature light chain variable region at least 90% identical to LG, an amino acid sequence of SEQ ID NO:8. In a further embodiment, the humanized antibody has a mature heavy chain variable region at least 95% identity to SEQ ID NO:18, and a mature light chain variable region at least 95% identity to SEQ ID NO:8. In another embodiment, positions H48, H66, H67, H69, H71 and H94 of the heavy chain variable region are occupied by I, K, A, L, A and S, and positions L22, L46, L69 and L71 of the light chain variable region are occupied by N, T, Q and Y. In some embodiments, any differences in CDRs of the mature heavy chain variable region and mature light variable region from SEQ ID NOS. 18 and 8 respectively reside in positions H60-H65.

In a further embodiment, the humanized antibody has CDRs of the mature heavy chain variable region that are identical to those of SEQ ID NO:18 and CDRs of the mature light chain variable region that are identical to those of SEQ ID NO:8. In one embodiment, the humanized antibody includes a mature heavy chain variable region having an amino acid sequence of SEQ ID NO:18 and a mature light chain variable region having an amino acid sequence of SEQ ID NO: 8.

In one embodiment, the humanized antibody is conjugated to a cytotoxic or cytostatic agent. In one embodiment, the humanized antibody is conjugated to a cytotoxic or cytostatic agent. In a further embodiment, the humanized antibody is conjugated to a cytotoxic agent. A cytotoxic agent can be, e.g., a DNA minor groove binder. A pyrrolo[1,4]benzodiazepine (PBD) is an example of a cytotoxic agent that is a DNA minor groove binder that can be conjugated to the humanized CD33 antibodies disclosed herein. In one embodiment, the PBD is conjugated to the CD33 antibody via an enzyme cleavable linker. In another embodiment, the cytotoxic agent has the formula wherein the wavy line indicates the site of attachment to the linker.

In another embodiment, the humanized antibody has an association constant for human or cynomolgus monkey CD33 of 0.5 to $2 \times 10^9$ $M^{-1}$.

In another embodiment, the humanized antibody has a mature heavy chain that is fused to a heavy chain constant region and a mature light chain that is fused to a light chain constant region. In a further embodiment, the heavy chain constant region is a mutant form of natural human constant region and has reduced binding to an Fcγ receptor relative to the natural human constant region. In another embodiment, the heavy chain constant region is of IgG1 isotype. Exemplary heavy chain constant region amino acid sequences include SEQ ID NO:27 and SEQ ID NO:29 (S239C). Exemplary light chain constant region amino acid sequences include SEQ ID NO:25.

In a further aspect, the invention provides a nucleic acid encoding any of the mature heavy or light chain variable regions described herein. Exemplary nucleic acids that encode heavy chain variable regions include SEQ ID NOs: 39-47; exemplary nucleic acids that encode light chain variable regions include SEQ ID NOs:32-38.

In one aspect, the invention provides methods of treating a patient having or at risk of having a cancer that expresses CD33, by administering to the patient an effective regime of a humanized antibody CD33 as disclosed herein. The CD33-expressing cancers include acute myeloid leukemia (AML), myelodysplastic syndrome (MDS), acute promyelocytic leukemia (APL), chronic myelogenous leukemia (CML), chronic myelomonocytic leukemia (CMML), a chronic myeloproliferative disorders, precursor B-cell acute lymphoblastic leukemia (preB-ALL), precursor T-cell acute lymphoblastic leukemia (preT-ALL), multiple myeloma (MM), mast cell disease, and myeloid Sarcoma. The humanized antibodies are preferably administered in a pharmaceutically suitable composition. In some embodiments, the administered humanized antibody is conjugated to a cytotoxic or cytostatic agent. In one embodiment, the administered humanized antibody is conjugated to a cytotoxic or cytostatic agent. In a further embodiment, the administered humanized antibody is conjugated to a cytotoxic agent. A cytotoxic agent can be, e.g., a DNA minor groove binder. A pyrrolo[1,4]benzodiazepine (PBD) is an example of a cytotoxic agent that is a DNA minor groove binder that can be conjugated to the administered humanized CD33 antibodies disclosed herein. In one embodiment, the PBD is conjugated to the administered CD33 antibody via an enzyme cleavable linker. In another embodiment, the cytotoxic agent has the formula

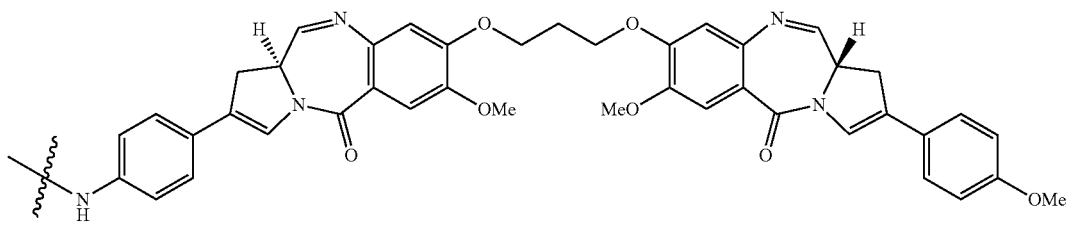 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

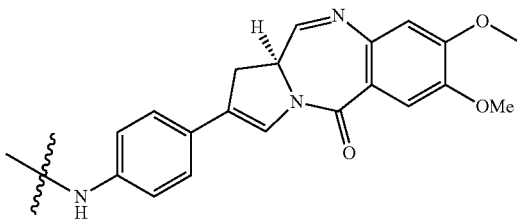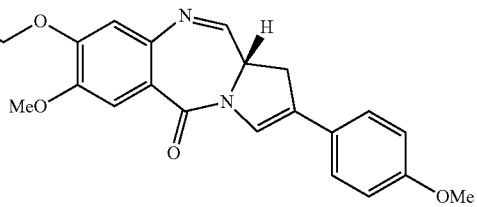

wherein the wavy line indicates the site of attachment to the linker.

BRIEF DESCRIPTION OF THE FIGURES

FIGS. 1A and 1B shows an alignment of the amino acid sequences of the parental murine mAb (referred to as m2H12) with the humanized 2H12 heavy (FIG. 1A, SEQ ID NO:9) and light chain variable (FIG. 1B, SEQ ID NO:1) regions.

DEFINITIONS

Figure 2:
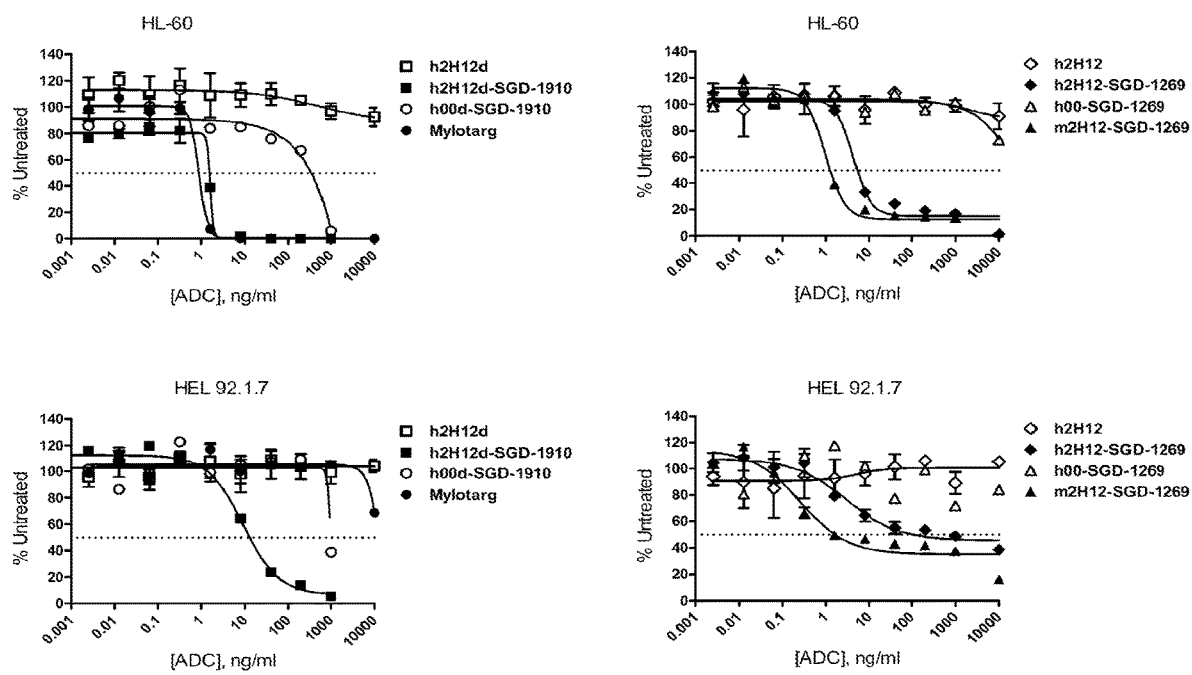
FIG. 2 shows the results of an in vitro cytotoxicity assay testing the activity of 2H12-derived antibody-drug conjugates (ADC) against the CD33-positive AML cell lines HL-60 and HEL 92.1.7. h2H12d was conjugated to SGD-1910; m2H12 and h2H12 were conjugated to SGD-1269. Non-binding control ADC (hOOd-SGD-1910 and h00-SGD-1269) were tested as a control of antigen specificity. MYLOTARG (gemtuzumab ozogamicin) is a well described CD33-directed antibody drug conjugate comprised of an anti-CD33 antibody hP67.6 linked to the cytotoxic drug calicheamicin and was also tested.

The invention provides, inter alia, monoclonal antibodies that specifically bind to the human CD33 protein and conjugates thereof. The antibodies are useful for treatment and diagnoses of CD33-expressing cancers as well as detecting the CD33 protein.

An "isolated" antibody refers to an antibody that has been identified and separated and/or recovered from components of its natural environment and/or an antibody that is recombinantly produced. A "purified antibody" is an antibody that is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Interfering proteins and other contaminants can include, for example, cellular components of the cells from which an antibody is isolated or recombinantly produced. Sometimes monoclonal antibodies are at least 60%, 70%, 80%, 90%, 95 or 99% w/w pure of interfering proteins and contaminants from production or purification. The antibodies described herein, including murine, chimeric, and humanized antibodies can be provided in isolated and/or purified form.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, for example, U.S. Pat. No. 4,816,567). The "monoclonal antibodies" may also be isolated from phage antibody libraries using the techniques described in Clackson et al. (1991) Nature, 352:624-628 and Marks et al. (1991) J. Mol. Biol., 222:581-597, for example or may be made by other methods. The antibodies described herein are monoclonal antibodies.

Specific binding of a monoclonal antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "antibody" includes an antibody by itself (naked antibody) or an antibody conjugated to a cytotoxic or cytostatic drug.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other. Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Antibodies that compete with the h2H12 antibody for binding to the human CD33 protein are included in this disclosure.

A 2H12 antibody is an antibody that specifically binds to the human CD33 protein, and that comprises three heavy chain complementarity determining regions (hCDRs): heavy chain CDR1, e.g., SEQ ID NO:19 or a sequence that is substantially identical to SEQ ID NO:19, heavy chain CDR2, e.g., SEQ ID NO:20 or a sequence that is substantially identical to SEQ ID NO:20, and heavy chain CDR3, e.g., SEQ ID NO:21 or a sequence that is substantially identical to SEQ ID NO:21; and three light chain CDRs: light chain CDR1, e.g., SEQ ID NO:22 or a sequence that is substantially identical to SEQ ID NO:22, light chain CDR2, e.g., SEQ ID NO:23 or a sequence that is substantially identical to SEQ ID NO:23, and light chain CDR3, e.g., SEQ ID NO:24 or a sequence that is substantially identical to SEQ ID NO:24. 2H12 antibodies include the murine 2H12 (m2H12) antibody and chimeric or humanized antibodies derived from the murine 2H12 antibody.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the CD33 targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by $CD16^+$ effector cells through the secretion of membrane pore-forming proteins and proteases, while phagocytosis is mediated by $CD32^+$ and $CD64^+$ effector cells (see *Fundamental Immunology*, 4$^{th}$ ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N.Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or the killing of a target cell. A "cytotoxic agent" refers to an agent that has a cytotoxic effect on a cell.

Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD33 antibody is administered to a subject.

The phrase "pharmaceutically acceptable salt," refers to pharmaceutically acceptable organic or inorganic salts of an anti-CD33-1 antibody or conjugate thereof or agent administered with an anti-CD33-1 antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, the term "about" encompasses values within a standard deviation of a stated value.

DETAILED DESCRIPTION

I. General

The invention provides monoclonal antibodies that specifically bind to CD33. The antibodies are useful for treatment and diagnoses of various cancers as well as detecting CD33.

II. Target Molecules

Unless otherwise indicated, CD33 means a human CD33. An exemplary human sequence is assigned Swiss Prot accession number P20138. P20138 is included herein as SEQ ID NO:55. P20138 includes a signal peptide, amino acids 1-17; an extra-cellular domain with IgG-like domains, amino acids 18-259; a transmembrane domain, amino acids 260-282; and a cytoplasmic domain, amino acids 283-364. Unless otherwise apparent from the context reference CD33 means at least an extracellular domain of the protein and usually the complete protein other than a cleavable signal peptide (amino acids 1-17 of P20138).

III. Antibodies of the Invention

A. Binding Specificity and Functional Properties

The invention provides a murine antibody, m2H12, and chimeric or humanized antibodies derived from m2H12. Murine antibodies were selected for ability to bind to both human CD33 protein and cynomolgus CD33 protein. Cynomolgus CD33 amino acid sequences are provided as SEQ ID NOs:56 and 57.

The affinity of humanized or chimeric forms of the murine m2H12 antibody (i.e., Ka) can bey greater than that of the m2H12 antibody, or within a factor of five or a factor of two (i.e., more than or less than) that of that of the murine antibody m2H12 for human CD33. One method of measuring affinity of an antibody for its target antigen is by determining an antibody's apparent dissociation constant. The present invention encompasses antibodies (e.g., chimeric and humanized forms of the mouse 2H12 antibody)

having an apparent dissociation constant that is essentially the same as that of murine 2H12 (i.e., within experimental error) as well as antibodies having a dissociation constant lower or higher than that of murine antibody 2H12 for human CD33. In some embodiments, antibodies of the present invention (e.g., chimeric, humanized and human forms of the mouse 2H12 antibody) have an apparent dissociation constant within a range of 0.1 to 10 times, or preferably within a range of 0.1 to 5 times, 0.1 to 2 times, or even 0.5 to 2 times that of the apparent dissociation constant of the murine 2H12 antibody for human CD33. In some aspects, the apparent dissociation constant (Kd) of the antibodies for human CD33 is preferably within a range of 0.1 nM to 50 nM, even more preferably within a range of 0.1 nM to 25 nM, even preferably within a range of 0.1 nM to 10 nM, 0.5 nM to 5 nM, or 0.5 nM to 2.5 nM. Humanized or chimeric m2H12 antibodies specifically bind to human CD33 in native form and/or recombinantly expressed from CHO cells as does the murine m2H12 antibody from which they were derived. Humanized or chimeric m2H12 antibodies bind to the same epitope and/or compete with m2H12 for binding to human CD33. In some embodiments, humanized or chimeric m2H12 antibodies also bind to the cyno-homolog of CD33, thus permitting preclinical testing in non-human primates.

Preferred antibodies (e.g., humanized or chimeric m2H12 antibodies) inhibit cancer (e.g., growth of cells, metastasis and/or lethality to the organisms) as shown on cancerous cells propagating in culture, in an animal model or clinical trial. Animal models can be formed by implanting CD33-expressing human tumor cell lines or primary patient tumor cells into appropriate immunodeficient rodent strains, e.g., athymic nude mice, NSG, or SCID mice. These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-CD33 antibodies or conjugated forms thereof as described in the Examples.

B. Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. A preferred acceptor sequence for the heavy chain is the germline $V_H$ exon $V_H$1-18 and for the J exon ($J_H$), exon $J_H$-6. For the light chain, a preferred acceptor sequence is exon $V_L$1-16 J exon Jκ-4. Thus, a humanized antibody is an antibody having some or all CDRs entirely or substantially from a non-human donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized or human antibody is substantially from or substantially identical to a corresponding CDR in a non-human antibody when at least 60%, 85%, 90%, 95% or 100% of corresponding residues (as defined by Kabat) are identical between the respective CDRs. In some embodiments, a CDR in a humanized antibody or human antibody is substantially from or substantially identical to a corresponding CDR in a non-human antibody when there are no more than 3 conservative amino acid substitutions in each CDR. The variable region framework sequences of an antibody chain or the constant region of an antibody chain are substantially from a human variable region framework sequence or human constant region respectively when at least 70%, 80%, 85%, 90%, 95% or 100% of corresponding residues defined by Kabat are identical. In some humanized antibodies of the present invention, there is at least one murine 2H12 backmutation in the heavy chain variable framework region of the antibody. Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., *J. Immunol.* 169:3076, 2002; Vajdos et al., *Journal of Molecular Biology,* 320: 415-428, 2002; Iwahashi et al., *Mol. Immunol.* 36:1079-1091, 1999; Tamura et al, *Journal of Immunology,* 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:
 (1) noncovalently binds antigen directly,
 (2) is adjacent to a CDR region,
 (3) otherwise interacts with a CDR region (e.g. is within about 6 Å of a CDR region); or
 (4) mediates interaction between the heavy and light chains.

The invention provides humanized forms of the mouse m2H12 antibody including nine exemplified humanized heavy chain mature variable regions (HA-HI) and seven exemplified humanized light chain mature variable regions (LA-LG). The permutations of these chains having the strongest binding (lowest EC50) are HCLA, HCLE, HCLG, HILA, HILE and HILG. Of these permutations, HILG (also known as h2H12) is preferred because it has the strongest binding.

The invention provides 2H12 antibodies in which the heavy chain variable region shows at least 90% identity to HA (SEQ ID NO:10) and a light chain variable region at least 90% identical to LA (SEQ ID NO:2). In some aspects, the antibody is a humanized antibody and there is at least one murine 2H12 backmutation in the heavy chain variable framework region. In other aspects, the antibody is a humanized antibody and there is at least one murine 2H12 backmutation in the light chain variable framework region. Additionally, the invention provides 2H12 antibodies in which the humanized heavy chain variable region shows at least 90%, 95%, 96%, 97%, 98% or 99% sequence identity to SEQ ID NOS:10-18 and the humanized light chain variable region shows at least 90%, 95%, 96%, 97%, 98% or 99% sequence identity to SEQ ID NOS: 2-8 (and any combinations thereof (i.e., the antibody can comprise any one of the heavy chain variable regions paired with any one of the light chain variable regions). For example, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the humanized light chain variable region shows at least 90%, 95%, 96%, 97%, 98%, 99% or 100% sequence identity to SEQ ID NOS:2, 3, 4, 5, 6, 7, or 8. In another embodiment, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the light chain variable region shows at least 90%, 95%, 96%, 97%, 98%, 99% or 100% sequence identity to SEQ ID NO:2. In another embodiment, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the light chain variable region shows at least 90%, 95%, 96%, 97%, 98%, 99% or 100% sequence identity to SEQ ID NO:3. In another embodiment, the invention provides antibodies in which the heavy chain variable region shows at least 90%, 95%, 96%, 97%, 98%. 99% or 100% sequence identity to SEQ ID NOS:10, 11, 12, 13, 14, 15, 16, 17, or 18, and the light chain variable region shows at least 90%, 95%, 96%, 97%, 98%, 99% or 100% sequence identity to SEQ ID NO:4. In another embodiment, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the light chain variable region shows at least 90%, 95%, 96%, 97%, 98%, 99% or 100% sequence identity to SEQ ID NO:5. In another embodiment, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the light chain variable region shows at least 90%, 95%, 96%, 97%, 98%. 99% or 100% sequence identity to SEQ ID NO:6. In another embodiment, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the light chain variable region shows at least 90%, 95%, 96%, 97%, 98%, 99% or 100% sequence identity to SEQ ID NO:7. In another embodiment, the invention provides antibodies in which the heavy chain variable region shows at least 90%, 95%, 96%, 97%, 98%, 99% or 100% sequence identity to SEQ ID NOS:10, 11, 12, 13, 14, 15, 16, 17, or 18, and the light chain variable region shows at least 90%, 95%, 96%, 97%, 98%, 99% or 100% sequence identity to SEQ ID NO:8.

In some aspects, these antibodies are humanized antibodies and some or all of the backmutations in the respective antibodies are retained. In some antibodies position H94 is occupied by S. In some antibodies, preferably, at least one of positions H48, H66, H67, H69, H71, and H94 is occupied by the amino acid from the corresponding position of the murine 2H12 antibody. Optionally, in any such antibody, position H48 is occupied by I; position H66 is occupied by K; position H67 is occupied by A; position H69 is occupied by L; position H71 is occupied by A; position H94 is occupied by S. In other embodiments in such antibodies, preferably, at least one of positions L22, L46, L69, and L71 is occupied by the amino acid from the corresponding position of the murine 2H12 antibody. Optionally, in any such antibody, position L22 is occupied by N; position L46 is occupied by T; position L69 is occupied by Q; and position L71 is occupied by Y.

Preferably, in any of the antibodies described above, e.g., 2H12 humanized antibodies in which the heavy chain variable region shows at least 90%, 95%, 96%, 97%, 98% or 99% sequence identity to SEQ ID NOS:10-18 and the light chain variable region shows at least 90%, 95%, 96%, 97%, 98% or 99% sequence identity to SEQ ID NOS:2-8, the CDR regions are identical or substantially identical to the CDR regions of the mouse donor antibody, i.e., murine 2H12 antibody (SEQ ID NOS:19-24). The CDR regions are as defined by Kabat. Antibodies of the present invention include antibodies HCLA, HCLE, HCLG, HILA, HILE, and HILG.

The invention provides variants of the HILG humanized antibody in which the humanized heavy chain mature variable region shows at least 90%, 95%, 96%, 97%, 98% or 99% identity to SEQ ID NO:18 and the humanized light chain mature variable region shows at least 90%, 95%, 96%, 97%, 98% or 99% sequence identity to SEQ ID NO:8. In some such antibodies, position H94 is occupied by S. Preferably, in such antibodies some or all of the backmutations in HILG are retained. In other words, at least 1, 2, 3, 4, 5, or preferably all 6 of heavy chain positions H48, H66, H67, H69, H71, and H94 are occupied by I and K and A and L and A and S, respectively. Also, at least 1, 2, 3, or preferably all 4 of light chain positions L22, L46, L69, and L71 are occupied by N and T and Q and Y respectively. The CDR regions of such humanized antibodies are preferably substantially identical to the CDR regions of HILG, which are the same as those of the mouse donor antibody. The CDR regions can be defined by any conventional definition (e.g., Chothia) but are preferably as defined by Kabat. In one embodiment, the humanized antibody comprises a heavy chain comprising the three CDRs of SEQ ID NO:18 and variable region frameworks with at least 95% identity to the variable region frameworks of SEQ ID NO:18. In another embodiment, the humanized antibody comprises a light chain comprising the three CDRs of SEQ ID NO:8 and variable region frameworks with at least 95% identity to variable region frameworks of SEQ ID NO:8. In a further embodiment, the humanized antibody comprises a heavy chain comprising the three CDRs of SEQ ID NO:18 and variable region frameworks with at least 95% identity to the variable region frameworks of SEQ ID NO:18, and a light chain comprising the three CDRs of SEQ ID NO:8, and variable region frameworks with at least 95% identity to the variable region frameworks of SEQ ID NO:8.

Insofar as humanized antibodies show any variation from the exemplified HILG humanized antibody, one possibility for such additional variation is additional backmutations in the variable region frameworks. Any or all of the positions backmutated in other exemplified humanized heavy or light chain mature variable regions can also be made (i.e., 1, 2, 3, 4, or all 5 of H38 occupied by N, H40 occupied by R, H73 occupied by K, H82A occupied by S, and H83 occupied by T in the heavy chain and 1 or both of L3 occupied by K, and L20 occupied by I in the light chain. However, such additional backmutations are not preferred because they in general do not improve affinity and introducing more mouse residues may give increased risk of immunogenicity.

Another possible variation is to substitute certain residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced HILG amino acids in the case of humanized 2H12 antibodies. Preferably, replacements relative to HILG (whether or not conservative) have no substantial effect on the binding affinity or potency of the humanized mAb, that is, its ability to bind human CD33 and inhibit growth of cancer cells.

Variants typically differ from the heavy and light chain mature variable region sequences of HILG (h2H12) by a small number (e.g., typically no more than 1, 2, 3, 5 or 10 in either the light chain or heavy chain mature variable region, or both) of replacements, deletions or insertions.

In some embodiments, humanized or chimeric antibodies have a CDR H2 with up to 1, 2, 3, 4, 5 or 6 substitutions, deletions or insertions relative to CDR H2 of heavy chain HI, and CDRs H1, H3, L1, L2 and L3, each have up to 1, 2, 3 or 4 substitutions, deletions or insertions relative to the corresponding CDR of heavy chain HI or light chain LG. In some embodiments, the humanized or chimeric antibodies of the invention have one or at most two conserved amino acid substitutions in amino acid(s) that are identified as part of a CDR. Examples of preferred amino acid substitutions include the following. In CDR1 of the light chain, an R residue can be substituted for a K at position 24; G, S, or T can be substituted for A at position 25; M can be substituted for L at position 33; and T can be substituted for S at position 34. In CDR2 of the light chain, a K residue can be substituted for an R residue at position 53; an M residue can be substituted for an L residue at position 54; an I residue can be substituted for a V residue at position 55; and an E residue can be substituted for a D residue at position 56. In CDR2 of the heavy chain, a D residue can be substituted for an E residue at position 61; an R residue can be substituted for a K residue at position 62; a Y residue can be substituted for an F residue at position 63; an R residue can be substituted for a K residue at position 64; and a G residue can be substituted for an A residue at position 65.

In some embodiments, the humanized antibodies of the invention comprise a mature heavy chain variable region of SEQ ID NO:18, with one two or three conservative substitutions in a CDR sequence as listed above. In some embodiments, the humanized antibodies of the invention comprise a mature light chain variable region of SEQ ID NO:8, with one two or three conservative substitutions in a CDR sequence as listed above.

C. Selection of Constant Region

Heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (numbering is according to the EU index (Kabat, *Sequences of Proteins of Immunological Interest* (National Institutes of Health, Bethesda, Md., 1987 and 1991); see US 20100158909, which is herein incorporated reference). The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. No. 6,624,821, U.S. Pat. No. 5,624,821.)

The in vivo half-life of an antibody can also impact its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human IgG1 involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human IgG1 enhance FcRn binding (Shields et al., 2001, *J. Biol. Chem.* 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Leu at position 428. EU numbering is used for all position in the constant region.

Oligosaccharides covalently attached to the conserved Asn297 are involved in the ability of the Fc region of an IgG to bind FcγR (Lund et al., 1996, *J. Immunol.* 157:4963-69; Wright and Morrison, 1997, *Trends Biotechnol.* 15:26-31). Engineering of this glycoform on IgG can significantly improve IgG-mediated ADCC. Addition of bisecting N-acetylglucosamine modifications (Umana et al., 1999, *Nat. Biotechnol.* 17:176-180; Davies et al., 2001, *Biotech. Bioeng.* 74:288-94) to this glycoform or removal of fucose (Shields et al., 2002, *J. Biol. Chem.* 277:26733-40; Shinkawa et al., 2003, *J. Biol. Chem.* 278:6591-604; Niwa et al., 2004, *Cancer Res.* 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, *J. Biol. Chem.* 276:6591-604). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, *J. Biol. Chem.* 276:6591-604; Okazaki et al., 2004, *J. Mol. Biol.* 336:1239-49).

Complement fixation activity of antibodies (both C1q binding and CDC activity) can be improved by substitutions at Lys326 and Glu333 (Idusogie et al., 2001, *J. Immunol.* 166:2571-2575). The same substitutions on a human IgG2 backbone can convert an antibody isotype that binds poorly to C1q and is severely deficient in complement activation activity to one that can both bind C1q and mediate CDC (Idusogie et al., 2001, *J. Immunol.* 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, *J. Immunol.* 154:2226-36). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, *J. Immunol.* 148:2918-22). In addition, a bispecific diabody construct with specificity for C1q also confers CDC activity (Kontermann et al., 1997, *Nat. Biotech.* 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity. Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P311S (see WO 06/036291). Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fc gamma receptor binding or increase binding to FcRN.

D. Expression of Recombinant Antibodies

Humanized or chimeric antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Human antibodies against CD33 protein can be provided by a variety of techniques described below. Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666; use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991) and phage display methods (see, e.g. Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332

Once expressed, antibodies can be purified according to standard procedures of the art, including HPLC purification, column chromatography, gel electrophoresis and the like (see generally, Scopes, *Protein Purification* (Springer-Verlag, NY, 1982)).

IV. Nucleic Acids

The invention further provides nucleic acids encoding any of the humanized heavy and light chains described above. Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In one embodiment, this disclosure provides an isolated polynucleotide encoding an antibody heavy chain variable region comprising the amino acid sequence of SEQ ID NO:18. This isolated polynucleotide can further encode a human IgG heavy chain constant region. The isotype of the IgG constant region is, e.g., IgG1, IgG2, IgG3, or IgG4. In one embodiment, the isotype of the IgG constant region is IgG1. In another embodiment, the encoded IgG1 constant region has an amino acid sequence comprising a substitution at residue 239, according to the Kabat numbering system, i.e., S239C. The disclosure also provides an expression vector comprising the isolated polynucleotide encoding the antibody heavy chain variable region comprising the amino acid sequence of SEQ ID NO:18, and further, a host cell comprising that expression vector. In some embodiments, the host cell is a mammalian host cell, e.g., a CHO cell.

In another embodiment, this disclosure provides an isolated polynucleotide encoding an antibody light chain variable region comprising the amino acid sequence of SEQ ID NO:8. This isolated polynucleotide can further encode a human IgG light chain constant region. The isotype of the IgG light chain constant region is, e.g., a kappa constant region. The disclosure also provides an expression vector comprising the isolated polynucleotide encoding the antibody light chain variable region comprising the amino acid sequence of SEQ ID NO:8, and further, a host cell comprising that expression vector. In some embodiments, the host cell is a mammalian host cell, e.g., a CHO cell. In another embodiment, this disclosure provides an isolated polynucleotide or polynucleotides encoding an antibody heavy chain variable region comprising the amino acid sequence of SEQ ID NO:18 and an antibody light chain variable region comprising the amino acid sequence of SEQ ID NO:8, the heavy chain variable domain and the light chain variable domain forming an antibody or antigen binding fragment that specifically binds to human CD33. This disclosure also provides an expression vector comprising the isolated polynucleotide or polynucleotides the encode the antibody heavy chain variable region comprising the amino acid sequence of SEQ ID NO:18 and the antibody light chain variable region comprising the amino acid sequence of SEQ ID NO:8. A host cell comprising the expression vector or vectors is also provided. The host cell is preferably a mammalian cell, e.g., a CHO cell.

In another embodiment, this disclosure provides first and second vectors comprising a polynucleotide encoding an antibody heavy chain variable region comprising the amino acid sequence of SEQ ID NO:18 and a polynucleotide encoding an antibody light chain variable region comprising the amino acid sequence of SEQ ID NO:8, the heavy chain variable domain and the light chain variable domain forming an antibody or antigen binding fragment that specifically binds to human CD33. Host cell comprising the vectors are provided, preferably mammalian host cells, such as a CHO cell.

V. Antibody Drug Conjugates

Anti-CD33 antibodies can be conjugated to cytotoxic moieties to form antibody-drug conjugates (ADCs). Particularly suitable moieties for conjugation to antibodies are cytotoxic agents (e.g., chemotherapeutic agents), prodrug converting enzymes, radioactive isotopes or compounds, or toxins (these moieties being collectively referred to as therapeutic agents or drugs). For example, an anti-CD33 antibody can be conjugated to a cytotoxic agent such as a chemotherapeutic agent, or a toxin (e.g., a cytostatic or cytocidal agent such as, e.g., abrin, ricin A, *pseudomonas* exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM1 and DM4), taxanes, benzodiazepines (e.g., pyrrolo[1,4]benzodiazepines (PBDs), indolinobenzodiazepines, and oxazolidinobenzodiazepines) and *vinca* alkaloids. Techniques for conjugating therapeutic agents to proteins, and in particular to antibodies, are well-known. (See, e.g., Alley et al., Current Opinion in Chemical Biology 2010 14:1-9; Senter, *Cancer J.*, 2008, 14(3):154-169.)

The therapeutic agent (e.g., cytotoxic agent) can be conjugated to the antibody in a manner that reduces its activity unless it is detached from the antibody (e.g., by hydrolysis, by antibody degradation, or by a cleaving agent). Such therapeutic agent can be attached to the antibody via a linker. A therapeutic agent conjugated to a linker is also referred to herein as a drug linker. The nature of the linker can vary widely. The components that make up the linker are chosen on the basis of their characteristics, which may be dictated in part, by the conditions at the site to which the conjugate is delivered.

The therapeutic agent can be attached to the antibody with a cleavable linker that is sensitive to cleavage in the intracellular environment of the anti-CD33-expressing cancer cell but is not substantially sensitive to the extracellular environment, such that the conjugate is cleaved from the antibody when it is internalized by the anti-CD33-expressing cancer cell (e.g., in the endosomal or, for example by virtue of pH sensitivity or protease sensitivity, in the lysosomal environment or in the caveolear environment). The therapeutic agent can also be attached to the antibody with a non-cleavable linker. As indicated, the linker may comprise a cleavable unit. In some such embodiments, the structure and/or sequence of the cleavable unit is selected such that it is cleaved by the action of enzymes present at the target site (e.g., the target cell). In other embodiments, cleavable units that are cleavable by changes in pH (e.g. acid or base labile), temperature or upon irradiation (e.g. photolabile) may also be used.

In some embodiments, the cleavable unit may comprise one amino acid or a contiguous sequence of amino acids. The amino acid sequence may be the target substrate for an enzyme.

In some aspects, the cleavable unit is a peptidyl unit and is at least two amino acids long. Cleaving agents can include cathepsins B and D and plasmin (see, e.g., Dubowchik and Walker, 1999, *Pharm. Therapeutics* 83:67-123). Most typical are cleavable unit that are cleavable by enzymes that are present in anti-CD33 expressing cells, i.e., an enzyme cleavable linker. Accordingly, the linker can be cleaved by an intracellular peptidase or protease enzyme, including a lysosomal or endosomal protease. For example, a linker that is cleavable by the thiol-dependent protease cathepsin-B, which is highly expressed in cancerous tissue, can be used (e.g., a linker comprising a Phe-Leu or a Val-Cit peptide or a Val-Ala peptide).

In some embodiments, the linker will comprise a cleavable unit (e.g., a peptidyl unit) and the cleavable unit will be directly conjugated to the therapeutic agent. In other embodiments, the cleavable unit will be conjugated to the therapeutic agent via an additional functional unit, e.g., a self-immolative spacer unit or a non-self-immolative spacer unit. A non self-immolative spacer unit is one in which part or all of the spacer unit remains bound to the drug unit after cleavage of a cleavable unit (e.g., amino acid) from the antibody drug conjugate. To liberate the drug, an independent hydrolysis reaction takes place within the target cell to cleave the spacer unit from the drug. With a self-immolative spacer unit, the drug is released without the need for drug for a separate hydrolysis step. In one embodiment, wherein the linker comprises a cleavable unit and a self immolative group, the cleavable unit is cleavable by the action of an enzyme and after cleavage of the cleavable unit, the self-immolative group(s) release the therapeutic agent. In some embodiments, the cleavable unit of the linker will be directly or indirectly conjugated to the therapeutic agent on one end and on the other end will be directly or indirectly conjugated to the antibody. In some such embodiments, the cleavable unit will be directly or indirectly (e.g., via a self-immolative or non-self-immolative spacer unit) conjugated to the therapeutic agent on one end and on the other end will be conjugated to the antibody via a stretcher unit. A stretcher unit links the antibody to the rest of the drug and/or drug linker. In one embodiment, the connection between the antibody and the rest of the drug or drug linker is via a maleimide group, e.g., via a maleimidocaproyl linker. In some embodiments, the antibody will be linked to the drug via a disulfide, for example the disulfide linked maytansinoid conjugates SPDB-DM4 and SPP-DM1.

The connection between the antibody and the linker can be via a number of different routes, e.g., through a thioether bond, through a disulfide bond, through an amide bond, or through an ester bond. In one embodiment, the connection between the anti-CD33 antibody and the linker is formed between a thiol group of a cysteine residue of the antibody and a maleimide group of the linker. In some embodiments, the interchain bonds of the antibody are converted to free thiol groups prior to reaction with the functional group of the linker. In some embodiments, a cysteine residue is an introduced into the heavy or light chain of an antibody and reacted with the linker. Positions for cysteine insertion by substitution in antibody heavy or light chains include those described in Published U.S. Application No. 2007-0092940 and International Patent Publication WO2008070593, each of which are incorporated by reference herein in its entirety and for all purposes.

In some embodiments, the antibody-drug conjugates have the following formula I:

$$L\text{-}(LU\text{-}D)_p \qquad (I)$$

wherein L is an anti-CD33 antibody, LU is a Linker unit and D is a Drug unit (i.e., the therapeutic agent). The subscript p ranges from 1 to 20. Such conjugates comprise an anti-CD33 antibody covalently linked to at least one drug via a linker. The Linker Unit is connected at one end to the antibody and at the other end to the drug.

The drug loading is represented by p, the number of drug molecules per antibody. Drug loading may range from 1 to 20 Drug units (D) per antibody. The skilled artisan will appreciate that in some aspects, the subscript p will range from 1 to 20 (i.e., both integer and non-integer values from 1 to 20). The skilled artisan will appreciate that in some aspects, the subscript p will be an integer from 1 to 20, and will represent the number of drug-linkers on a singular antibody. In other aspects, p represents the average number of drug-linker molecules per antibody, e.g., the average number of drug-linkers per antibody in a reaction mixture or composition (e.g., pharmaceutical composition), and can be an integer or non-integer value. Accordingly, in some aspects, for compositions (e.g., pharmaceutical compositions), p represents the average drug loading of the antibody-drug conjugates in the composition, and p ranges from 1 to 20.

In some embodiments, p is from about 1 to about 8 drugs per antibody. In some embodiments, p is 1. In some embodiments, p is 2. In some embodiments, p is from about 2 to about 8 drugs per antibody. In some embodiments, p is from about 2 to about 6, 2 to about 5, or 2 to about 4 drugs per antibody. In some embodiments, p is about 2, about 4, about 6 or about 8 drugs per antibody.

The average number of drugs per antibody unit in a preparation from a conjugation reaction may be characterized by conventional means such as mass spectroscopy, ELISA assay, HIC, and HPLC. The quantitative distribution of conjugates in terms of p may also be determined.

Exemplary antibody-drug conjugates include auristatin based antibody-drug conjugates, i.e., conjugates wherein the drug component is an auristatin drug. Auristatins bind tubulin, have been shown to interfere with microtubule dynamics and nuclear and cellular division, and have anticancer activity. Typically the auristatin based antibody-drug conjugate comprises a linker between the auristatin drug and the anti-CD33 antibody. The auristatins can be linked to the anti-CD33 antibody at any position suitable for conjugation to a linker. The linker can be, for example, a cleavable linker (e.g., a peptidyl linker) or a non-cleavable linker (e.g., linker released by degradation of the antibody). The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include MMAF (monomethyl auristatin F), and MMAE (monomethyl auristatin E). The synthesis and structure of exemplary auristatins are described in U.S. Pat. Nos. 7,659,241, 7,498,298, 2009-0111756, 2009-0018086, and 7,968,687 each of which is incorporated herein by reference in its entirety and for all purposes.

Exemplary auristatin based antibody-drug conjugates include vcMMAE, vcMMAF and mcMMAF antibody-drug conjugates as shown below wherein Ab is an antibody as described herein and val-cit represents the valine-citrulline dipeptide:

Exemplary antibody-drug conjugates include PBD based antibody-drug conjugates; i.e., antibody-drug conjugates wherein the drug component is a PBD drug.

PBDs are of the general structure:

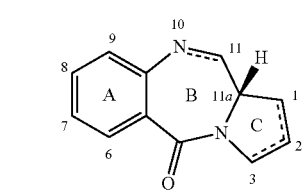

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the

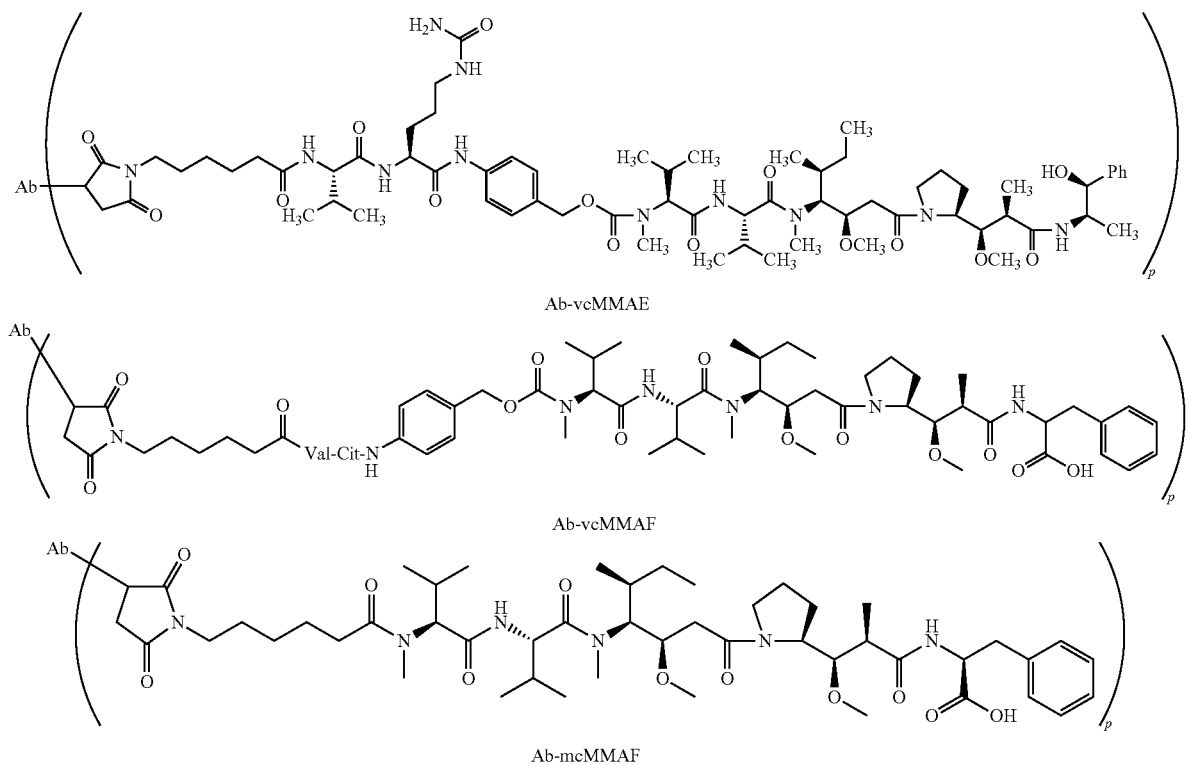

Ab-vcMMAE

Ab-vcMMAF

Ab-mcMMAF or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the linker via a sulfur atom of a cysteine residue. In some aspects, the cysteine residue is one that is engineered into the antibody. In other aspects, the cysteine residue is an interchain disulfide cysteine residue.

N10-C11 position, which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumor agents.

The biological activity of these molecules can be potentiated by joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand cross-link which is thought to be mainly responsible for their biological activity.

In some embodiments, PBD based antibody-drug conjugates comprise a PBD dimer linked to an anti-CD33 antibody. The monomers that form the PBD dimer can be the same or different, i.e., symmetrical or unsymmetrical. The PBD dimer can be linked to the anti-CD33 antibody at any position suitable for conjugation to a linker. For example, in some embodiments, the PBD dimer will have a substituent at the C2 position that provides an anchor for linking the compound to the anti-CD33 antibody. In alternative embodiments, the N10 position of the PBD dimer will provide the anchor for linking the compound to the anti-CD33 antibody.

Typically the PBD based antibody-drug conjugate comprises a linker between the PBD drug and the anti-CD33 antibody. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in International Application No. WO 2011/130613 and is as follows wherein the wavy line indicates the site of attachment to the linker:

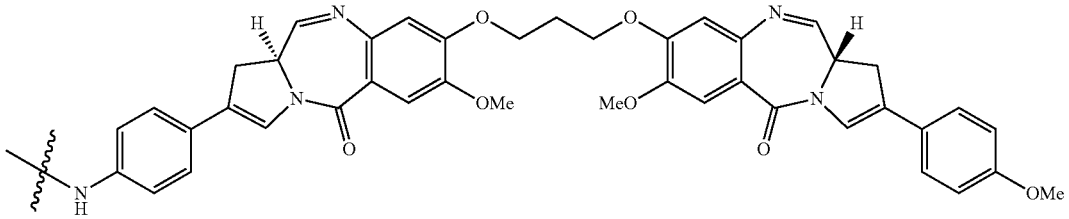 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

or a pharmaceutically acceptable salt thereof. An exemplary linker is as follows wherein the wavy line indicates the site of attachment to the drug and the antibody is linked via the maleimide group.

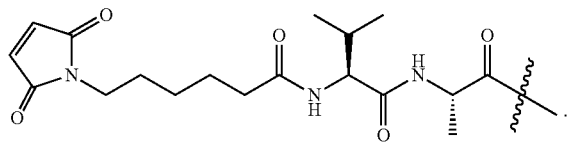 [SMILES: *C(=O)[C@H](C)NC(=O)[C@@H](NC(=O)CCCCCN1C(=O)C=CC1=O)C(C)C]

Exemplary PBDs based antibody-drug conjugates include antibody-drug conjugates as shown below wherein Ab is an antibody as described herein:

or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the drug linker via a sulfur atom of a cysteine residue that is engineered into the antibody. In some aspects, the cysteine residue is engineered into the antibody at position 239 (IgG1) as determined by the EU index (Kabat, *Sequences of Proteins of Immunological Interest* (National Institutes of Health, Bethesda, Md., 1987 and 1991).

VI. Other Antibodies to CD33

As well as humanized forms of the m2H12 antibodies discussed above, other antibodies binding to an extracellular domain of CD33 can be used in some of the methods of the invention, particularly the treatment of cancer. Chimeric or veneered forms of these antibodies can be made by conventional methods summarized below.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

Any of the antibodies can be selected to have the same or overlapping epitope specificity as an exemplar antibody,

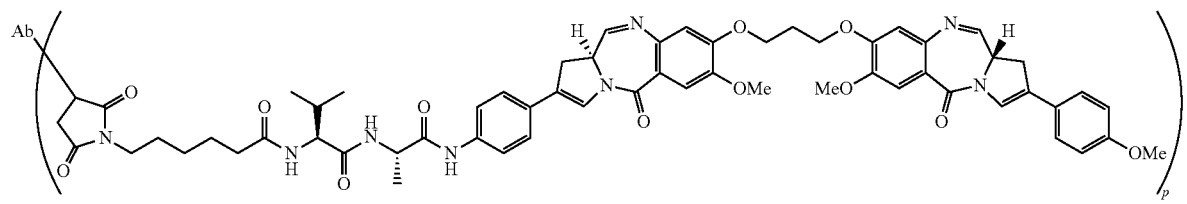

such as the m2H12 antibody, by a competitive binding assay, such as described in the Examples, or otherwise. Preferred antibodies have the same epitope specificity as the m2H12 antibody. Those of skill are able to identify an epitope bound by an antibody using a variety of methods. For example, array-based oligopeptide scanning or pepscan analysis uses a library of oligo-peptide sequences from overlapping and non-overlapping segments of a target antigen and tests for their ability to bind the antibody of interest. See, e.g., Geysen et al., PNAS 81:3998-4002 (1984). Non-linear epitopes can be identified using, e.g., CLIPS™ technology, a variation of array-based oligopeptide scanning. See, e.g., Timmerman et al., Open Vaccine J. 2:56-67 (2009). The antigen protein can also be mutagenized and then use to assess binding by the antibody of interest. The protein systematic site-directed mutagenesis can be used or a library of mutations can be made and used to screen for antibody binding. Mutation libraries can be purchased from, e.g., Integral Molecular. Amide hydrogen/deuterium exchange MS can be used to identify epitopes. Antigens of interest are placed in deuterated water and labeled with deuterons. The protein is then digested with a protease and the resulting peptide fragments are subjected to mass spec analysis. The antigen is also assessed in the presence of an antibody and differences in labeling of peptide fragments indicate areas of antibody binding.

VII. Therapeutic Applications

Antibodies derived from the murine 2H12 antibody, e.g., chimeric or humanized antibodies, alone or as CD33 antibody drug conjugates thereof, can be used to treat cancer. Some such cancers show detectable levels of CD33 measured at either the protein (e.g., by immunoassay using one of the exemplified antibodies) or mRNA level. Some such cancers show elevated levels of CD33 relative to noncancerous tissue of the same type, preferably from the same patient. An exemplary level of CD33 on cancer cells amenable to treatment is 5000-150000 CD33 molecules per cell, although higher or lower levels can be treated. Optionally, a level of CD33 in a cancer is measured before performing treatment.

Examples of cancers associated with CD33 expression and amenable to treatment include myeloid diseases such as, acute myeloid leukemia (AML), chronic myeloid leukemia (CML), other myeloproliferative disorders, including chronic myelomonocytic leukemia and chronic myeloproliferative disorders, acute promyelocytic leukemia (APL), thrombocytic leukemia, a myelodysplastic syndrome, precursor B-cell acute lymphoblastic leukemia (preB-ALL), precursor T-cell acute lymphoblastic leukemia (preT-ALL), multiple myeloma (MM), mast cell disease including mast cell leukemia and mast cell sarcoma, myeloid sarcomas, refractory anemia, a preleukemia syndrome, a lymphoid leukemia, or an undifferentiated leukemia. The treatment can also be applied to patients who are treatment naïve, who are refractory to conventional treatments (e.g., chemotherapy or MYLOTARG® (gemtuzumab ozogamicin), or who have relapsed following a response to such treatments.

CD33 antibodies derived from the murine 2H12 antibody, including chimeric antibodies or humanized antibodies such as h2H12 antibodies, can be used to treat cancers that express CD33 protein. In one embodiment, a humanized antibody derived from murine 2H12 antibody is used to treat a subject with CD33-positive acute myeloid leukemia (AML). In a further embodiment, the h2H12 antibody is used to treat a subject with CD33-positive AML. In another embodiment, a humanized antibody derived from murine 2H12 antibody is used to treat a subject with CD33-positive chronic myeloid leukemia (CML). In a further embodiment, the h2H12 antibody is used to treat a subject with CD33-positive CML. In another embodiment, a humanized antibody derived from murine 2H12 antibody is used to treat a subject with CD33-positive chronic myelomonocytic leukemia (CMML). In a further embodiment, the h2H12 antibody is used to treat a subject with CD33-positive chronic CMML. In another embodiment, a humanized antibody derived from murine 2H12 antibody is used to treat a subject with CD33-positive thyroid leukemia. In a further embodiment, the h2H12 antibody is used to treat a subject with CD33-positive thyroid leukemia. In another embodiment, a humanized antibody derived from murine 2H12 antibody is used to treat a subject with CD33-positive myelodysplastic syndrome. In a further embodiment, the h2H12 antibody is used to treat a subject with CD33-positive myelodysplastic syndrome. In another embodiment, a humanized antibody derived from murine 2H12 antibody is used to treat a subject with CD33-positive myeloproliferative disorder. In a further embodiment, the h2H12 antibody is used to treat a subject with CD33-positive myeloproliferative disorder. In another embodiment, a humanized antibody derived from murine 2H12 antibody is used to treat a subject with CD33-positive refractory anemia. In a further embodiment, the h2H12 antibody is used to treat a subject with CD33-positive refractory anemia. In another embodiment, a humanized antibody derived from murine 2H12 antibody is used to treat a subject with CD33-positive preleukemia syndrome. In a further embodiment, the h2H12 antibody is used to treat a subject with CD33-positive preleukemia syndrome. In another embodiment, a humanized antibody derived from murine 2H12 antibody is used to treat a subject with CD33-positive lymphoid leukemia. In a further embodiment, the h2H12 antibody is used to treat a subject with CD33-positive lymphoid leukemia. In another embodiment, a humanized antibody derived from murine 2H12 antibody is used to treat a subject with CD33-positive undifferentiated leukemia. In a further embodiment, the h2H12 antibody is used to treat a subject with CD33-positive undifferentiated leukemia. In one embodiment, a humanized antibody derived from murine 2H12 antibody is used to treat a subject with CD33-positive precursor B-cell acute lymphoblastic leukemia (preB-ALL). In a further embodiment, the h2H12 antibody is used to treat a subject with CD33-positive pre-B-ALL. In one embodiment, a humanized antibody derived from murine 2H12 antibody is used to treat a subject with CD33-positive precursor T-cell acute lymphoblastic leukemia (preT-ALL). In a further embodiment, the h2H12 antibody is used to treat a subject with CD33-positive preT-ALL. In one embodiment, a humanized antibody derived from murine 2H12 antibody is used to treat a subject with CD33-positive multiple myeloma (MM). In a further embodiment, the h2H12 antibody is used to treat a subject with CD33-positive MM. In one embodiment, a humanized antibody derived from murine 2H12 antibody is used to treat a subject with CD33-positive mast cell disease including mast cell leukemia and mast cell sarcoma. In a further embodiment, the h2H12 antibody is used to treat a subject with CD33-positive mast cell disease including mast cell leukemia and mast cell sarcoma.

The CD33 antibody can be, for example, an unconjugated or conjugated antibody, e.g., a CD33 antibody drug conjugate. In some embodiments, the anti-CD33 antibody can be a humanized or chimeric 2H12 antibody. In some embodiments, the anti-CD33 antibody can be an antibody that competes with a murine, humanized, or chimeric 2H12 antibody for specific binding to CD33.

CD33 antibodies derived from murine 2H12 antibody, including chimeric antibodies or humanized antibodies such as h2H12, can be conjugated to a therapeutic agent and used to treat subjects with CD33-positive cancers. Examples of therapeutic agents are provided herein, including active therapeutic agents, e.g., auristatins, and highly active therapeutic agents, e.g., PBDs. An h2H12 antibody conjugated to an active therapeutic agent, i.e., an h2H12 antibody-drug conjugate (ADC), can be used to treat a subject with CD33-positive cancer. An h2H12 antibody conjugated to an auristatin can be used to treat a subject with CD33-positive cancer. An h2H12 antibody conjugated to a highly active therapeutic agent can be used to treat a subject with CD33-positive cancer. An h2H12 antibody conjugated to a PBD can be used to treat a subject with CD33-positive cancer.

Some cancer cells develop resistance to a therapeutic agent after increasing expression of a protein increases efflux of the therapeutic agent out of the cancer cell. Such proteins include P-glycoprotein, multidrug resistance-associated protein, lung resistance-related protein, and breast cancer resistance protein. Detection of drug resistance in cancer cells can be performed by those of skill. Antibodies or assays that detect efflux proteins are commercially available from, e.g., Promega, Millipore, Abcam, and Sigma-Aldrich. In one embodiment, an antibody derived from a murine 2H12 antibody is used to treat a subject with a multi-drug resistant cancer, e.g., a CD33-positive multi-drug resistant cancer. In another embodiment a humanized antibody derived from the murine 2H12 antibody is used to treat a subject with a multidrug resistant cancer, e.g., a CD33-positive multi-drug resistant cancer. In one embodiment, an h2H12 antibody is used to treat a subject with a multi-drug resistant cancer, e.g., a CD33-positive multi-drug resistant cancer. In a further embodiment, an h2H12 ADC is used to treat a subject with a multi-drug resistant cancer, e.g., a CD33-positive multi-drug resistant cancer. In another embodiment, an h2H12 antibody conjugated to a highly active therapeutic agent is used to treat a subject with a multi-drug resistant cancer, e.g., a CD33-positive multi-drug resistant cancer. In another embodiment, an h2H12 antibody conjugated to a PBD is used to treat a subject with a multi-drug resistant cancer, e.g., a CD33-positive multi-drug resistant cancer. In a further embodiment, an h2H12 antibody conjugated to a PBD is used to treat a subject with a multi-drug resistant, CD33-positive acute myeloid leukemia (AML).

Humanized or chimeric antibodies derived from the murine 2H12 antibody, alone or as drug-conjugates thereof, are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the cancer relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg 1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for active monoclonal antibody drug conjugates thereof, e.g., auristatins, are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. Exemplary dosages for highly active monoclonal antibody drug conjugates thereof, e.g., PBDs, are 1.0 µg/kg to 1.0 mg/kg, or 1.0 µg/kg to 500.0 µg/kg of the subject's body weight. In some methods, the patient is administered then antibody or ADC every two, three or four weeks. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or antibody-drug conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between once weekly or once monthly over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient. Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 0.01-10 mg/ml, such as 1.0 mg/ml.

Treatment with antibodies of the invention can be combined with chemotherapy, radiation, stem cell treatment, surgery other treatments effective against the disorder being treated. Useful classes of other agents that can be administered with humanized antibodies to CD33 include, for example, antibodies to other receptors expressed on cancerous cells, antitubulin agents (e.g., auristatins), DNA minor groove binders (e.g., PBDs), DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with an antibody derived from murine 2H12 antibody, e.g., a chimeric antibody, a humanized antibody, or the h2H12 antibody, optionally in combination with any of the other agents or regimes described above alone or as an antibody drug conjugate, can increase the median progression-free survival or overall survival time of patients with cancer (e.g., ALL, CML, CMML), especially when relapsed or refractory, by at least 30% or 40% but preferably 50%, 60% to 70% or even 100% or longer, compared to the same treatment (e.g., chemotherapy) but without the antibody derived from murine 2H12 antibody, alone or as an antibody-drug conjugate. In addition or alternatively, treatment (e.g., standard chemotherapy) including the antibody derived from murine 2H12 antibody, alone or as an antibody-drug conjugate, can increase the complete response rate, partial response rate, or objective response rate (complete+partial) of patients with tumors by at least 30% or 40% but preferably 50%, 60% to 70% or even 100% compared to the same treatment (e.g., chemotherapy) but without the antibody derived from murine 2H12 antibody.

Typically, in a clinical trial (e.g., a phase II, phase II/III or phase III trial), the aforementioned increases in median progression-free survival and/or response rate of the patients treated with standard therapy plus the antibody derived from murine 2H12 antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

VIII. Other Applications

The anti-CD33 antibodies disclosed herein can be used for detecting CD33 in the context of clinical diagnosis or treatment or in research. Expression of CD33 on a cancer provides an indication that the cancer is amenable to treatment with the antibodies of the present invention. The antibodies can also be sold as research reagents for laboratory research in detecting cells bearing CD33 and their response to various stimuli. In such uses, monoclonal antibodies can be labeled with fluorescent molecules, spin-labeled molecules, enzymes or radioisotopes, and can be provided in the form of kit with all the necessary reagents to perform the assay for CD33. The antibodies described herein, m2h12 and chimeric or humanized versions thereof, e.g., h2H12, can be used to detect CD33 protein expression and determine whether a cancer is amenable to treatment with CD33 ADCs. As an example, murine 2H12 and chimeric or humanized versions thereof, e.g., h2H12, can be used to detect CD33 expression on lymphocytes, lymphoblasts, monocytes, myelomonocytes or other CD33-expressing cells. The antibodies can also be used to purify CD33 protein, e.g., by affinity chromatography.

Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

I. Generation of Anti-CD33 Antibodies

Materials

Cell lines described in the following examples were maintained in culture according to the conditions specified by the American Type Culture Collection (ATCC) (Manassas, Va.) or the Deutsche Sammlung von Mikroorganismen und Zellkulturen GmbH (DSMZ), (Braunschweig, Germany). Primary AML cells were maintained in Iscove's Modified Dulbecco's medium (IMDM) containing 20% heat-inactivated FBS, supplemented with 25 ng/ml each of granulocyte-macrophage-colony-stimulating factor (GM-CSF), granulocyte-colony-stimulating factor (G-CSF), interleukin-3 (IL-3) and stem cell factor (SCF). Cell culture reagents were obtained from Invitrogen Corp (Carlsbad, Calif.) and cytokines were purchased from PeproTech (Rocky Hill, N.J.).

Methodologies:

Saturation Binding Assays

One hundred thousand CD33-positive cells (HL-60, HEL 92.1.7, and HEK-293F cells transfected to express human or cynomologus CD33) were transferred to 96-well plates. AlexaFluor-647 labeled CD33 mAb was added in concentrations ranging from 50 nM to 0.85 pM and the cells incubated on ice for 30 minutes. Cells were pelleted by centrifugation, washed 3 times with a PBS+1% BSA solution, and resuspended in 125 µL of PBS+1% BSA. Fluorescence was analyzed using a flow cytometer, and the percent of saturated fluorescent signal was used to determine percent bound and to subsequently calculate apparent Kd.

Competition Binding Assays

One hundred thousand CD33-positive cells were transferred to 96-well plates and incubated for 1 hour on ice with 1 nM AlexaFluor-647 labeled m2H12 and increasing concentrations (from 0.03 nM to 600 nM) of unlabeled hybrid, humanized or chimeric 2H12 mAb. Cells were centrifuged, washed 3 times with PBS, and resuspended in 125 µL of a PBS+1% BSA solution. Fluorescence was analyzed using a flow cytometer, and the percent of saturated fluorescent signal was used to determine percent labeled 2H12 mAb bound. The EC50 was extrapolated by fitting the data to a sigmoidal dose-response curve with variable slope.

Cytotoxicity Assay

AML cell lines or primary AML cells were treated with CD33-specific mAb and antibody drug conjugates (ADC) for 96 hours at 37° C. In some experiments, non-antigen binding ADC were included as negative controls. Cell viability for the cell lines was measured using CelltiterGlo (Promega Corporation, Madison, Wis.) according to the manufacturer's instructions. Cells were incubated for 25 minutes at room temperature with the CelltiterGlo reagents and luminescence was measured on a Fusion HT fluorescent plate reader (Perkin Elmer, Waltham, Mass.). For the primary AML cells, viability was measured by flow cytometry using Annexin V and propidium iodide staining. Results are reported as IC50, the concentration of compound needed to yield a 50% reduction in viability compared to vehicle-treated cells (control=100%).

Production of Antibody Drug Conjugates

Antibody drug conjugates of the CD33 antibodies were prepared as described in U.S. 20050238649 and WO2011/130613 using the anti-CD33 antibodies described herein. The drug linker SGD-1269 (mcMMAF) is described in U.S.20050238649 and the drug linker SGD-1910 is described WO2011/130613. Preparation of cysteine mutants of IgG1 mAb is generally described in US20100158909. The drug-linker SGD-1269 was conjugated to the anti-CD33 antibody h2H12 via a thiol group of a cysteine residue of an interchain disulfide bond and the average drug load was about 4 drugs per antibody. The drug-linker SGD-1910 was conjugated to the anti-CD33 antibody via a thiol group of a cysteine residue introduced at position 239 of the IgG1 chain of the antibody and the average drug load was about 2 drugs per antibody. Antibodies with cysteine at the 239 position carry the designation EC, e.g., h2H12EC or h00EC In Vivo Activity Study Disseminated AML Model CB-17/IcrHsd-PrkdcSCID (SCID) mice were inoculated intravenously with $5 \times 10^6$ HL-60 tumor cells in the tail vein. One day post tumor inoculation, mice (n=8/group) were untreated or dosed intraperitoneally every four days for a total of two doses with CD33 mAb and ADC or non-binding control mAb and ADC. Mylotarg dosed intraperitoneally every seven days for a total of two doses was included as a positive control in this Mylotarg-sensitive AML model. Animals were euthanized when body weight loss was ≥20%, or when mice showed signs of disseminated disease manifested as central nervous system symptoms that included cranial swelling and/or hind limb paralysis, or development of a palpable disseminated tumor mass.

Subcutaneous AML Models

SCID mice were inoculated subcutaneously with $5 \times 10^6$ HL-60 or TF1-α AML tumor cells. Tumor growth was monitored with calipers and the mean tumor volume was calculated using the formula ($0.5 \times$[length$\times$width$^2$]). When the mean tumor volume reached approximately 100 mm$^3$, mice (n=6-7/group) were untreated or dosed intraperitoneally with a single dose of CD33 ADC or non-binding control ADC. For the HL-60 model, mice were treated with human IVIg (single intraperitoneal injection of 10 mg/kg) approximately four hours prior to administration of the therapeutic antibody to minimize interaction of the test ADC with Fc receptors on AML cells. Mice were euthanized when tumor volumes reached approximately 1000 mm$^3$. All animal procedures were performed under a protocol approved by the Institutional Animal Care and Use Committee in a facility accredited by the Association for Assessment and Accreditation of Laboratory Animal Care.

Results

1. Generation of Murine CD33 mAb

Antibodies directed against the human CD33 antigen were generated in Balb/c mice by immunization with recombinant human CD33-Fc fusion protein. The murine mAb 2H12 (m2H12) was selected based upon binding affinity for human CD33 and cynomologus CD33 to permit preclinical testing in nonhuman primates.

2. Design and Testing of Humanized Antibodies

Humanized antibodies were derived from the murine 2H12 antibody. Nine humanized heavy chains (HA-HI) and seven humanized light chains (LA-LG) were made incorporating back mutations at different positions. See, FIGS. 1A, B a sequence alignment and Tables 1-4.

TABLE 1

Humanizing Mutations in Heavy Chain Variants

| $V_H$ Variant | $V_H$ Exon Acceptor Sequence | Donor Framework Residues |
|---|---|---|
| hV$_H$A | VH1-18 | None |
| hV$_H$B | VH1-18 | H71 |
| hV$_H$C | VH1-18 | H94 |
| hV$_H$D | VH1-18 | H73 |
| hV$_H$E | VH1-18 | H48 |
| hV$_H$F | VH1-18 | H38, H40 |
| hV$_H$G | VH1-18 | H66, H67, H69 |
| hV$_H$H | VH1-18 | H82A, H83 |
| hV$_H$I | VH1-18 | H48, H66, H67, H69, H71, H94 |

TABLE 2

Humanizing Mutations in Light Chain Variants

| $V_L$ Variant | $V_L$ Exon Acceptor Sequence | Donor Framework Residues |
|---|---|---|
| hV$_L$A | VL1-16 | None |
| hV$_L$B | VL1-16 | L3 |
| hV$_L$C | VL1-16 | L46 |
| hV$_L$D | VL1-16 | L69 |
| hV$_L$E | VL1-16 | L71 |
| hV$_L$F | VL1-16 | L20, L22 |
| hV$_L$G | VL1-16 | L22, L46, L69, L71 |

TABLE 3

Specific Mutations in 2H12 Heavy Chain Variants

| Variant | H38 | H40 | H48 | H66 | H67 | H69 | H71 | H73 | H82A | H83 | H94 |
|---|---|---|---|---|---|---|---|---|---|---|---|
| HA | R | A | M | R | V | M | T | T | R | R | R |
| HB | R | A | M | R | V | M | A* | T | R | R | R |
| HC | R | A | M | R | V | M | T | T | R | R | S* |
| HD | R | A | M | R | V | M | T | K* | R | R | R |
| HE | R | A | I* | R | V | M | T | T | R | R | R |
| HF | N* | R* | M | R | V | M | T | T | R | R | R |

TABLE 3-continued

Specific Mutations in 2H12 Heavy Chain Variants

| Variant | H38 | H40 | H48 | H66 | H67 | H69 | H71 | H73 | H82A | H83 | H94 |
|---------|-----|-----|-----|-----|-----|-----|-----|-----|------|-----|-----|
| HG | R | A | M | K* | A* | L* | T | T | R | R | R |
| HH | R | A | M | R | V | M | T | T | S* | T* | R |
| HI | R | A | I* | K* | A* | L* | A* | T | R | R | S* |

*Mouse residues

TABLE 4

Specific Mutations in 2H12 Light Chain Variants

| Variant | L3 | L20 | L22 | L46 | L69 | L71 |
|---------|----|----|-----|-----|-----|-----|
| LA | Q | T | T | S | T | F |
| LB | K* | T | T | S | T | F |
| LC | Q | T | T | T* | T | F |
| LD | Q | T | T | S | Q* | F |
| LE | Q | T | T | S | T | Y* |
| LF | Q | I* | N* | S | T | F |
| LG | Q | T | N* | T* | Q* | Y* |

*Mouse residues

Humanized heavy and light chains were paired with chimeric light and heavy chains (chimeric chains composed of murine variable regions and human constant regions) respectively. The humanized/chimeric hybrid variants of CD33 mAb were tested for binding to human CD33 expressed on the surface of HEL 92.1.7 AML cells (Table 5). Heavy chains HC and HI were selected for further study. Humanized antibodies were expressed representing permutations of humanized heavy chains HC and HI and humanized light chains LA, LE and LG and binding to cells expressing human or cynomolgus (cyno) CD33 was determined (Table 6). The HILG antibody (2H12 HILG) was selected as the humanized antibody that most closely resembled the binding characteristics of the murine CD33 mAb m2H12. The HILG antibody is referred to as the h2H12 antibody (human 2H12 antibody). The $K_D$ for m2H12, h2H12, and h2H12 with an S239C mutation (EU numbering) in the IgG1 heavy chain (referred to as h2H12EC, for engineered cysteine), was determined for human CD33 expressed as an endogenous protein in two AML cell lines or as a recombinant protein in a HEK293F cell line. The $K_D$ for these antibodies was also determined for cyno CD33 expressed as a recombinant protein in a HEK293F cell line (Table 7).

TABLE 5

EC50 Binding Determinations for Chimeric-Humanized Hybrid CD33 mAb Variants on CD33-Expressing HEL9217 AML Cells

| mAb | EC50 (nM) |
|-----|-----------|
| m2H12 | 2.38 |
| c2H12 | 1.97 |
| cHLA | 2.61 |
| cHLB | 2.53 |
| cHLC | 2.49 |
| cHLD | 2.48 |
| cHLE | 1.95 |
| cHLF | 2.02 |
| cHLG | 1.91 |
| HAcL | DNB |
| HBcL | DNB |
| HCcL | 2.95 |
| HDcL | DNB |
| HEcL | DNB |
| HFcL | DNB |
| HGcL | DNB |
| HHcL | DNB |
| HIcL | 2.56 |
| HILG | 3.39 |

DNB, did not bind;
m, murine;
cH, chimeric heavy chain;
cL, chimeric light chain

TABLE 6

EC50 Binding Determinations for Humanized CD33 mAb Variants on Human CD33 and Cyno CD33-Expressing Cells

| 2H12 Variant | HEL9217 EC50 (nM) | HEK293F humanCD33 EC50 (nM) | HEK293F cynoCD33 EC50 (nM) |
|---|---|---|---|
| m2H12 | 5.4 | 11.6 | 30.6 |
| HCLA | 13.6 | 31.7 | 141.4 |
| HCLE | 12.8 | 22.2 | 129.3 |
| HCLG | 7.9 | 17.9 | 63 |
| HILA | 12.2 | 26.8 | 126.4 |
| HILE | 11.1 | 19.3 | 64.8 |
| HILG | 7.8 | 14.4 | 39.9 |

TABLE 7

Affinity Measurements of Humanized CD33 mAbs for Human and Cyno CD33-Expressing Cells

| | HL-60 | HEL9217 | HEK293F-hCD33 | HEK293F-cyno CD33 |
|---|---|---|---|---|
| m2H12 | 0.144 | 0.170 | ND | 2.718 |
| h2H12 | 0.208 | 0.161 | 0.958 | 1.218 |
| h2H12EC | 0.253 | 0.204 | 1.000 | 5.128 |

ND, not done

In Vitro Anti-Tumor Activity of h2H12 ADC

The cytotoxic activity of h2H12 antibody-drug conjugates was tested using two drug linker systems, SGD-1269 (auristatin drug-linker) and SGD-1910 (pyrrolobenzodiazapine dimer drug-linker). A cytotoxicity assay was performed against two CD33-positive AML cell lines, HL-60 and HEL 92.1.7, using unconjugated antibody, h2H12-ADCs and control ADCs that do not bind to CD33. As shown in FIG. 2, h2H12 and h2H12EC (also referred to as h2H12d) unconjugated antibodies had no activity against either cell line. Likewise, the non-binding control ADCs (h00EC-SGD-1910 and h00-SGD-1269) were not cytotoxic. In contrast, h2H12EC-SGD-1910 was cytotoxic towards HL-60 (IC50~1.6 ng/mL) and HEL 92.1.7 (IC50~12.9 ng/mL). The activity of the h2H12EC-SGD-1910 was similar to that of Mylotarg, a well described anti-CD33 directed antibody drug conjugate, on HL-60 cells and more potent when tested against HEL 92.1.7 (a multi-drug resistant (MDR) cell line), where Mylotarg is ineffective. m2H12-SGD-1269 and h2H12-SGD-1269 were active against HL-60 cells (IC50 of 1.3 ng/mL and 5.3 ng/mL respectively) and to a lesser extent HEL 92.1.7 (FIG. 2). In separate experiments, h2H12-SGD-1269 and h2H12EC-SGD-1910 were further tested against an expanded panel of CD33-positive AML cell lines. As shown in Table 8, h2H12-SGD-1269 was active against 4 of 7 AML cell lines (mean IC50 for responsive cell lines, 72.8 mg/mL), and h2H12EC-SGD-1910 had potent activity against 7 of 7 AML cell lines tested (mean IC50, 20.4 ng/mL). h2H12EC-SGD-1910 was more potent than Mylotarg, which was active in 3 of 8 CD33-positive AML cell lines. No activity was observed when the ADCs were tested against three cell lines that were not of AML origin and did not express CD33 (Table 8). Altogether, these data demonstrate that h2H12 and h2H12EC antibody drug conjugates selectively target CD33-positive cells and display cytotoxic activity towards those cells.

TABLE 8

In vitro activity of h2H12 drug conjugates and Mylotarg against AML cell lines

| Cell Line | Cell Type | CD33 Receptor Number ($\times 10^3$) | MDR Status | IC50 (ng/mL) | | |
|---|---|---|---|---|---|---|
| | | | | h2H12-SGD-1269 | h2H12EC-SGD-1910 | Mylotarg |
| HL-60 | AML | 17 | − | 2 | 1 | 11 |
| U937 | AML | 20 | +/− | 19 | 22 | >1000 |
| MV4-11 | AML | 18 | +/− | 0.1 | 0.1 | 6 |
| KG-1 | AML | 23 | + | 270 | 3 | 3 |
| HEL 92.1.7 | AML | 19 | + | >1000 | 7 | >1000 |
| TF-1 | AML | 6 | + | >1000 | 61 | >1000 |
| TF1-α | AML | 17 | + | >1000 | 49 | >1000 |
| Ramos | NHL | 0 | NT | >10,000 | >1000 | NT |
| ES-2 | Ovarian Carcino. | 0 | NT | >10,000 | >1000 | 300 |
| SKOV-3 | Ovarian Carcino. | 0 | NT | >10,000 | >5000 | 10,000 |

MDR, multi-drug resistance;
+, dye efflux > 2-fold above background;
NT, not tested In Vivo Anti-Tumor Activity of h2H12 ADC The activity of h2H12-SGD-1269 was tested in a model in which the HL-60 AML cell line was introduced into SCID mice to initiate disseminated disease. Mice were treated the next day with h2H12 antibody, non-specific IVIg negative control antibody, h2H12-SGD-1269, a non-binding control ADC (hBU12-SGD-1269) or Mylotarg according to the dose levels and schedule described in Table 9. The median survival of HL-60-innoculated mice increased from 22 days in the untreated or human IVIg-treated groups to 29 days (p=0.007), 41 days (p=0.001) and 52 days (p<0.001) in groups receiving h2H12 (3 mg/kg) and 1 or 3 mg/kg h2H12-SGD-1269 respectively (Table 9). h2H12EC-SGD-1269 prolonged survival similar to that of mice dosed with h2H12-SGD-1269 (median survival of 50 and 52 days respectively). Mylotarg was also active in this MDR-negative model; greater than 50% of the Mylotarg-treated mice survived to the end of the study on day 99. Survival of mice treated with the unconjugated antibody h2H12 or the non-binding control ADC (hBU12-SGD-1269) was prolonged 6-7 days compared to untreated control mice, but to a much lesser extent than mice treated with the CD33-targeted ADC.

TABLE 9

Activity of h2H12-SGD-1269 drug conjugate in disseminated HL-60 AML xenograft model

| | Dose Level (mg/kg) | Dose Schedule | Median Survival (Day) | P Value |
|---|---|---|---|---|
| Untreated | — | — | 22 | — |
| hIVIg | 3 | Every 4 days, 2 doses | 22 | NS[1] |
| h2H12 | 3 | Every 4 days, 2 doses | 29 | 0.007[2] |
| h2H12-SGD-1269 | 1 | Every 4 days, 2 doses | 41 | 0.001[3] |
| h2H12-SGD-1269 | 3 | Every 4 days, 2 doses | 52 | <0.001[3] |
| h2H12EC-SGD-1269 | 3 | Every 4 days, 2 doses | 50 | <0.001[3] |

TABLE 9-continued

Activity of h2H12-SGD-1269 drug conjugate in disseminated HL-60 AML xenograft model

| | Dose Level (mg/kg) | Dose Schedule | Median Survival (Day) | P Value |
|---|---|---|---|---|
| hBU12-SGD-1269 | 3 | Every 4 days, 2 doses | 28 | <0.001[2] |
| Mylotarg | 3 | Every 7 days, 2 doses | NR | <0.001[2] |

[1]Test versus untreated
[2]Test versus hIVIg
[3]Test versus hBU12-SGD-1269 (non-binding control ADC)
NS, not significant;
NR, not reached;
—, not applicable
hIVIG, human intravenous immunoglobulin;
hBU12-SGD-1269, non-binding control ADC.

The activity of h2H12EC-SGD-1910 was tested in two subcutaneous AML xenograft models, HL-60 and TF1-α. SCID mice bearing established (~100 mm³) tumors were dosed with h2H12EC-SGD-1910 or non-binding control ADC (h00EC-SGD-1910) as described in Table 10 for the HL-60 model and in Table 11 for the TF1-αtumor model. Treatment with h2H12EC-SGD-1910 significantly decreased tumor growth compared to untreated and non-binding control ADC-treated mice as measured by the median time for tumors to quadruple in volume (Tables 10 and 11). The anti-tumor activity observed with CD33-targeted ADC was dose dependent. For HL-60 tumors, a single dose of 0.1 mg/kg resulted in complete and durable tumor regression in 6 of 6 treated mice. A lower dose of 0.03 mg/kg resulted in complete regression in 1 of 6 treated mice and extended the time to tumor quadrupling to 20 days compared to 15 days for untreated mice and those similarly dosed with the non-binding control ADC (h00d-SGD-1910). In the MDR-positive TF1-αtumor model (Table 11), a single dose of 0.3 mg/kg h2H12EC-SGD-1910 resulted in complete and durable tumor regression in 5 of 7 treated mice. The median day to tumor quadrupling had not been reached by the end of the study on day 117. In contrast, the tumors in mice similarly dosed with the non-binding control ADC (h00EC-SGD-1910) had quadrupled in volume by 27 days. Likewise, the median time for tumors to quadruple in mice dosed with 0.1 mg/kg or 0.03 mg/kg h2H12EC-SGD-1910 was significantly longer (p=0.0001) than that of untreated or h00EC-SGD-1910 treated mice. Mylotarg was not active in the TE1-α tumor model; tumor growth of Mylotarg-treated mice was not different than untreated mice. Taken together, the data demonstrate that h2H12-ADC show anti-tumor activity in AML xenograft models that is dose-dependent and significantly greater than non-targeted ADC.

TABLE 10

Activity of h2H12EC-SGD-1910 drug conjugate in subcutaneous HL-60 AML xenograft model

| | Dose Level, Single Dose (mg/kg) | Median Time to Quadruple (Day) | P value: Test versus Untreated | P value: Test versus Control ADC | DCR |
|---|---|---|---|---|---|
| Untreated | — | 15 | — | — | 0/6 |
| hIVIg | 10 | 15 | — | — | 0/6 |
| h2H12EC-SGD-1910 | 0.1 | NR | 0.0005 | 0.0005 | 6/6 |
| h2H12EC-SGD-1910 | 0.03 | 20 | 0.0005 | 0.0016 | 1/6 |
| h00EC-SGD-1910 | 0.1 | 17 | 0.009 | — | 0/6 |
| h00EC-SGD-1910 | 0.03 | 15 | NS | — | 0/6 |

NS, not significant;
NR, not reached;
—, not applicable;
hIVIg, human intravenous immunoglobulin (administered 4 hours prior to dosing ADC);
h00EC-SGD-1910, non-binding control ADC;
DCR, durable complete response (no measureable tumor at the end of study on day 50)

TABLE 11

Activity of h2H12EC-SGD-1910 drug conjugate in subcutaneous TF1-ccAML xenograft model

| | Dose Level, Single Dose (mg/kg) | Median Time to Quadruple (Day) | P value: Test versus Untreated | P value: Test versus Control ADC | DCR |
|---|---|---|---|---|---|
| Untreated | — | 20 | — | — | 0/7 |
| h2H12EC-SGD-1910 | 0.3 | NR | 0.0001 | 0.0001 | 5/7 |
| h2H12EC-SGD-1910 | 0.1 | 51 | 0.0001 | 0.0001 | 0/7 |
| h2H12EC-SGD-1910 | 0.03 | 32 | 0.0001 | 0.0001 | 0/7 |
| h00EC-SGD-1910 | 0.3 | 27 | 0.001 | — | 0/7 |
| h00EC-SGD-1910 | 0.1 | 23 | 0.03 | — | 0/7 |
| h00EC-SGD-1910 | 0.03 | 22 | 0.05 | — | 0/7 |
| Mylotarg | 1 | 21 | NS | — | 0/7 |

NS, not significant;
NR, not reached;
—, not applicable;
h00EC-SGD-1910, non-binding control ADC;
DCR, durable complete response (no measureable tumor at the end of the study on day 117)

What is claimed is:

1. A nucleic acid or nucleic acids encoding a mature heavy chain variable region and a mature light chain variable region wherein the mature heavy chain variable region comprises three heavy chain complementarity determining regions (CDRs): heavy chain CDR1 consisting of SEQ ID NO:19, heavy chain CDR2 consisting of SEQ ID NO:20, and heavy chain CDR3 consisting of SEQ ID NO:21; and the mature light chain variable region comprises three light chain CDRs: light chain CDR1 consisting of SEQ ID NO:22, light chain CDR2 consisting of SEQ ID NO:23, and light chain CDR3 consisting of SEQ ID NO:24, wherein an antibody comprising the mature heavy chain variable region and the mature light chain variable region specifically binds to human CD33.

2. The nucleic acid or nucleic acids of claim 1, wherein the mature heavy chain and mature light chain variable region are from a murine antibody, a chimeric antibody, or a humanized antibody.

3. The nucleic acid or nucleic acids of claim 2, wherein the antibody is a humanized antibody.

4. The nucleic acid or nucleic acids of claim 1, wherein the mature heavy chain variable region has an amino acid sequence at least 90% identical to SEQ ID NO:18 and the mature light chain variable region at least 90% identical to SEQ ID NO:8.

5. The nucleic acid or nucleic acids of claim 4, provided that position H94 is occupied by S.

6. The nucleic acid or nucleic acids of claim 1, wherein the mature heavy chain variable region has an amino acid sequence at least 90% identical to SEQ ID NO:18 provided that position H48 is occupied by I, position H66 is occupied by K, position H67 is occupied by A, position H69 is occupied by L, position H71 is occupied by A, and position H94 is occupied by S and the mature light chain variable region has at least 90% identical to SEQ ID NO:8 provided position L22 is occupied by N, position L46 is occupied by T, position L69 is occupied by Q, and position L71 by Y, as determined by the Kabat numbering system.

7. The nucleic acid or nucleic acids of claim 1 wherein the mature heavy chain variable region has an amino acid sequence at least 95% identical to SEQ ID NO:18 and the mature light chain variable region has an amino acid sequence at least 95% identical to SEQ ID NO:8.

8. The nucleic acid or nucleic acids of claim 1, wherein the mature heavy chain variable region has an amino acid sequence designated SEQ ID NO:18 and the mature light chain variable region has an amino acid sequence designated SEQ ID NO:8.

9. The nucleic acid or nucleic acids of claim 8, wherein the nucleic acid or nucleic acids encodes the mature heavy chain variable region fused to a heavy chain constant region, and the mature light chain variable region fused to a light chain constant region.

10. The nucleic acid or nucleic acids of claim 9, wherein the heavy chain constant region is a mutant form of natural human constant region which has reduced binding to an Fcγ receptor relative to the natural human constant region.

11. The nucleic acid or nucleic acids of claim 9, wherein the heavy chain constant region is of human IgG1 isotype.

12. The nucleic acid or nucleic acids of claim 9, wherein the heavy chain constant region has an amino acid sequence comprising SEQ ID NO:27 and the light chain constant region has an amino acid sequence comprising SEQ ID NO:25.

13. The nucleic acid or nucleic acids of claim 9, wherein the heavy chain constant region has an amino acid sequence comprising SEQ ID NO:29 and the light chain constant region has an amino acid sequence comprising SEQ ID NO:25.

14. A nucleic acid encoding a mature heavy chain variable region and a mature light chain variable region of an antibody specifically binding to human CD33, the nucleic acid having a nucleic acid sequence comprising SEQ ID NO:47 encoding the mature heavy chain and SEQ ID NO:38 encoding the mature light chain.

15. The nucleic acid of claim 14, wherein the nucleic acid sequence further comprises SEQ ID NO:49 encoding a heavy chain constant region fused to the mature heavy chain variable region and SEQ ID NO:48 encoding a light chain constant region fused to the mature light chain variable region.

16. The nucleic acid of claim 14, wherein the nucleic acid sequence further comprises SEQ ID NO:51 encoding a heavy chain constant region fused to the mature heavy chain variable region and SEQ ID NO:48 encoding a light chain constant region fused to the mature light chain variable region.

17. A vector comprising the nucleic acid or vectors comprising the nucleic acids of claim 1.

18. A cell line comprising the vector or vectors of claim 17.

19. A method of expressing an antibody, comprising culturing the cell line of claim 18, wherein the antibody comprising the mature heavy chain and mature light chain is expressed.

20. Nucleic acids respectively encoding a mature heavy chain variable region and a mature light chain variable region of an antibody specifically binding to human CD33, the nucleic acid encoding the mature heavy chain variable region having a nucleic acid sequence comprising SEQ ID NO:47 and the nucleic acid encoding the mature light chain variable region having a nucleic acid sequence comprising SEQ ID NO:38.

21. The nucleic acids of claim 20, wherein the nucleic acid encoding the mature heavy chain variable region further comprises SEQ ID NO:49 encoding a heavy chain constant region fused to the mature heavy chain variable region and the nucleic acid encoding the mature light chain variable region further comprises SEQ ID NO:48 encoding a light chain constant region fused to the mature light chain variable region.

22. The nucleic acids of claim 20, wherein the nucleic acid sequence encoding the mature heavy chain variable region further comprises SEQ ID NO:51 encoding a heavy chain constant region fused to the mature heavy chain variable region and the nucleic acid encoding the mature light chain variable region further comprises SEQ ID NO:48 encoding a light chain constant region fused to the mature light chain variable region.

23. A method of making an antibody, comprising expressing the nucleic acid or nucleic acids of claim 1.

24. A method of making an antibody, comprising expressing the nucleic acids of claim 20.

* * * * *

SEQUENCE LISTING

```
<160> NUMBER OF SEQ ID NOS: 57

<210> SEQ ID NO 1
<211> LENGTH: 107
<212> TYPE: PRT
<213> ORGANISM: Mus musculus

<400> SEQUENCE: 1

Asp Ile Lys Met Thr Gln Ser Pro Ser Ser Met Tyr Ala Ser Leu Gly
1               5                   10                  15

Glu Arg Val Ile Ile Asn Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45
```

```
Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Leu
                 85                  90                  95

Thr Phe Gly Ala Gly Thr Lys Leu Glu Leu Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Synthesized

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
                 20                  25                  30

Leu Ser Trp Phe Gln Gln Lys Pro Gly Lys Ala Pro Lys Ser Leu Ile
             35                  40                  45

Tyr Arg Ala Asn Arg Leu Val Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Leu
                 85                  90                  95

Thr Phe Gly Gly Gly Thr Lys Val Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Synthesized

<400> SEQUENCE: 3

Asp Ile Lys Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
                 20                  25                  30

Leu Ser Trp Phe Gln Gln Lys Pro Gly Lys Ala Pro Lys Ser Leu Ile
             35                  40                  45

Tyr Arg Ala Asn Arg Leu Val Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Leu
                 85                  90                  95

Thr Phe Gly Gly Gly Thr Lys Val Glu Ile Lys
            100                 105

<210> SEQ ID NO 4
<211> LENGTH: 107
<212> TYPE: PRT
<213> ORGANISM: Artificial Sequence
```

<220> FEATURE:
<223> OTHER INFORMATION: Synthesized

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: Synthesized

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
50                  55                  60

-continued

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Synthesized

<400> SEQUENCE: 7

Asp Ile Gln Met Thr Gln Ser Pro Ser Ser Leu Ser Ala Ser Val Gly
1               5                   10                  15

Asp Arg Val Ile Ile Asn Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Synthesized

<400> SEQUENCE: 8

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 9
<211> LENGTH: 117
<212> TYPE: PRT
<213> ORGANISM: Mus musculus

<400> SEQUENCE: 9

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Synthesized

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Glu Asp Ala Met Asp Tyr Trp Gly Gln Gly Thr Thr
            100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Synthesized

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Ala Arg Val Thr Met Thr Ala Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Glu Asp Ala Met Asp Tyr Trp Gly Gln Gly Thr Thr
                100                 105                 110

Val Thr Val Ser Ser
        115

<210> SEQ ID NO 12
<211> LENGTH: 117
<212> TYPE: PRT
<213> ORGANISM: Artificial Sequence
<220> FEATURE:
<223> OTHER INFORMATION: Synthesized

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Asp Ile Asn Trp Val Arg Gln Ala Pro Gly Gln Gly Leu Glu Trp Met
            35                  40                  45

Gly Trp Ile Tyr Pro Gly Asp Gly Ser Thr Lys Tyr Asn Glu Lys Phe
    50                  55                  60

Lys Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
                100                 105                 110

Val Thr Val Ser Ser
        115

<210> SEQ ID NO 13
<211> LENGTH: 117
<212> TYPE: PRT
<213> ORGANISM: Artificial Sequence
<220> FEATURE:
<223> OTHER INFORMATION: Synthesized

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Asp Ile Asn Trp Val Arg Gln Ala Pro Gly Gln Gly Leu Glu Trp Met
            35                  40                  45

Gly Trp Ile Tyr Pro Gly Asp Gly Ser Thr Lys Tyr Asn Glu Lys Phe
    50                  55                  60

Lys Ala Arg Val Thr Met Thr Thr Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Glu Asp Ala Met Asp Tyr Trp Gly Gln Gly Thr Thr
                100                 105                 110

Val Thr Val Ser Ser

<210> SEQ ID NO 14
<211> LENGTH: 117
<212> TYPE: PRT
<213> ORGANISM: Artificial Sequence
<220> FEATURE:
<223> OTHER INFORMATION: Synthesized

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Glu Asp Ala Met Asp Tyr Trp Gly Gln Gly Thr Thr
            100                 105                 110

Val Thr Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: Synthesized

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Glu Asp Ala Met Asp Tyr Trp Gly Gln Gly Thr Thr
            100                 105                 110

Val Thr Val Ser Ser
        115

<210> SEQ ID NO 16
<211> LENGTH: 117
<212> TYPE: PRT
<213> ORGANISM: Artificial Sequence
<220> FEATURE:
<223> OTHER INFORMATION: Synthesized

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Glu Asp Ala Met Asp Tyr Trp Gly Gln Gly Thr Thr
            100                 105                 110

Val Thr Val Ser Ser
        115

<210> SEQ ID NO 17
<211> LENGTH: 117
<212> TYPE: PRT
<213> ORGANISM: Artificial Sequence
<220> FEATURE:
<223> OTHER INFORMATION: Synthesized

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Ala Arg Val Thr Met Thr Thr Asp Thr Ser Thr Ser Thr Ala Tyr
65                  70                  75                  80

Met Glu Leu Ser Ser Leu Thr Ser Asp Asp Thr Ala Val Tyr Tyr Cys
                85                  90                  95

Ala Arg Gly Tyr Glu Asp Ala Met Asp Tyr Trp Gly Gln Gly Thr Thr
            100                 105                 110

Val Thr Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: Synthesized

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe

```
                    50                  55                  60
Lys Ala Lys Ala Thr Leu Thr Ala Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Ser Gly Tyr Glu Asp Ala Met Asp Tyr Trp Gly Gln Gly Thr Thr
            100                 105                 110

Val Thr Val Ser Ser
            115

<210> SEQ ID NO 19
<211> LENGTH: 5
<212> TYPE: PRT
<213> ORGANISM: Mus musculus

<400> SEQUENCE: 19

Asn Tyr Asp Ile Asn
1               5

<210> SEQ ID NO 20
<211> LENGTH: 17
<212> TYPE: PRT
<213> ORGANISM: Mus musculus

<400> SEQUENCE: 20

Trp Ile Tyr Pro Gly Asp Gly Ser Thr Lys Tyr Asn Glu Lys Phe Lys
1               5                   10                  15

Ala

<210> SEQ ID NO 21
<211> LENGTH: 8
<212> TYPE: PRT
<213> ORGANISM: Mus musculus

<400> SEQUENCE: 21

Gly Tyr Glu Asp Ala Met Asp Tyr
1               5

<210> SEQ ID NO 22
<211> LENGTH: 11
<212> TYPE: PRT
<213> ORGANISM: Mus musculus

<400> SEQUENCE: 22

Lys Ala Ser Gln Asp Ile Asn Ser Tyr Leu Ser
1               5                   10

<210> SEQ ID NO 23
<211> LENGTH: 7
<212> TYPE: PRT
<213> ORGANISM: Mus musculus

<400> SEQUENCE: 23

Arg Ala Asn Arg Leu Val Asp
1               5

<210> SEQ ID NO 24
<211> LENGTH: 9
<212> TYPE: PRT
<213> ORGANISM: Mus musculus

<400> SEQUENCE: 24
```

Leu Gln Tyr Asp Glu Phe Pro Leu Thr
1               5

<210> SEQ ID NO 25
<211> LENGTH: 106
<212> TYPE: PRT
<213> ORGANISM: Homo sapiens

<400> SEQUENCE: 25

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 329
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 28
<211> LENGTH: 330
<212> TYPE: PRT
<213> ORGANISM: Artificial Sequence
<220> FEATURE:
<223> OTHER INFORMATION: Synthesized

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 329
<212> TYPE: PRT
<213> ORGANISM: Artificial Sequence
<220> FEATURE:
<223> OTHER INFORMATION: Synthesized

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly
            325

<210> SEQ ID NO 30
<211> LENGTH: 22
<212> TYPE: PRT
<213> ORGANISM: Artificial Sequence
<220> FEATURE:
<223> OTHER INFORMATION: Synthesized

<400> SEQUENCE: 30

Met Asp Met Arg Thr Pro Ala Gln Phe Leu Gly Ile Leu Leu Leu Trp
1               5                   10                  15

Phe Pro Gly Ile Lys Cys
            20

<210> SEQ ID NO 31
<211> LENGTH: 19
<212> TYPE: PRT
<213> ORGANISM: Artificial Sequence
<220> FEATURE:
<223> OTHER INFORMATION: Synthesized

<400> SEQUENCE: 31

Met Gly Trp Arg Trp Ile Phe Leu Phe Leu Leu Ser Gly Thr Ala Gly
1               5                   10                  15

Val His Cys

<210> SEQ ID NO 32
<211> LENGTH: 321
<212> TYPE: DNA
<213> ORGANISM: Artificial Sequence
<220> FEATURE:
<223> OTHER INFORMATION: Synthesized

<400> SEQUENCE: 32
gacatccaga tgacccagtc tccatcctca ctgtctgcat ctgtaggaga cagagtcacc      60
atcacttgta aggctagtca ggacattaat agctatttga ctggtttca gcagaaacca     120 gggaaagccc ctaagtccct gatctataga gcaaatagat tggtagatgg ggtcccatca    180
aggttctctg gcagtggatc tgggacagat ttcactctca ccatcagcag cctgcagcct    240
gaagattttg caacttatta ctgcttgcag tatgatgagt ttcctctcac atttggagga    300
gggaccaagg tggagatcaa a                                              321

<210> SEQ ID NO 33
<211> LENGTH: 321
<212> TYPE: DNA
<213> ORGANISM: Artificial Sequence
<220> FEATURE:
<223> OTHER INFORMATION: Synthesized

<400> SEQUENCE: 33
gacatcaaga tgacccagtc tccatcctca ctgtctgcat ctgtaggaga cagagtcacc      60
atcacttgta aggctagtca ggacattaat agctatttga ctggtttca gcagaaacca     120 gggaaagccc ctaagtccct gatctataga gcaaatagat tggtagatgg ggtcccatca    180
aggttctctg gcagtggatc tgggacagat ttcactctca ccatcagcag cctgcagcct    240
gaagattttg caacttatta ctgcttgcag tatgatgagt ttcctctcac atttggagga    300
gggaccaagg tggagatcaa a                                              321
```

<210> SEQ ID NO 34
<211> LENGTH: 321
<212> TYPE: DNA
<213> ORGANISM: Artificial Sequence
<220> FEATURE:
<223> OTHER INFORMATION: Synthesized

<400> SEQUENCE: 34

```
gacatccaga tgacccagtc tccatcctca ctgtctgcat ctgtaggaga cagagtcacc    60
atcacttgta aggctagtca ggacattaat agctatttga gctggtttca gcagaaacca   120
gggaaagccc ctaagaccct gatctataga gcaaatagat tggtagatgg ggtcccatca   180
aggttctctg gcagtggatc tgggacagat ttcactctca ccatcagcag cctgcagcct   240
gaagattttg caacttatta ctgcttgcag tatgatgagt ttcctctcac atttggagga   300
gggaccaagg tggagatcaa a                                             321
```

<210> SEQ ID NO 35
<211> LENGTH: 321
<212> TYPE: DNA
<213> ORGANISM: Artificial Sequence
<220> FEATURE:
<223> OTHER INFORMATION: Synthesized

<400> SEQUENCE: 35

```
gacatccaga tgacccagtc tccatcctca ctgtctgcat ctgtaggaga cagagtcacc    60
atcacttgta aggctagtca ggacattaat agctatttga gctggtttca gcagaaacca   120
gggaaagccc ctaagtccct gatctataga gcaaatagat tggtagatgg ggtcccatca   180
aggttctctg gcagtggatc tgggcaagat ttcactctca ccatcagcag cctgcagcct   240
gaagattttg caacttatta ctgcttgcag tatgatgagt ttcctctcac atttggagga   300
gggaccaagg tggagatcaa a                                             321
```

<210> SEQ ID NO 36
<211> LENGTH: 321
<212> TYPE: DNA
<213> ORGANISM: Artificial Sequence
<220> FEATURE:
<223> OTHER INFORMATION: Synthesized

<400> SEQUENCE: 36

```
gacatccaga tgacccagtc tccatcctca ctgtctgcat ctgtaggaga cagagtcacc    60
atcacttgta aggctagtca ggacattaat agctatttga gctggtttca gcagaaacca   120
gggaaagccc ctaagtccct gatctataga gcaaatagat tggtagatgg ggtcccatca   180
aggttctctg gcagtggatc tgggacagat tatactctca ccatcagcag cctgcagcct   240
gaagattttg caacttatta ctgcttgcag tatgatgagt ttcctctcac atttggagga   300
gggaccaagg tggagatcaa a                                             321
```

<210> SEQ ID NO 37
<211> LENGTH: 321
<212> TYPE: DNA
<213> ORGANISM: Artificial Sequence
<220> FEATURE:
<223> OTHER INFORMATION: Synthesized

<400> SEQUENCE: 37

```
gacatccaga tgacccagtc tccatcctca ctgtctgcat ctgtaggaga cagagtcatt    60
atcaattgta aggctagtca ggacattaat agctatttga gctggtttca gcagaaacca   120
```

```
gggaaagccc ctaagtccct gatctataga gcaaatagat tggtagatgg ggtcccatca      180
aggttctctg gcagtggatc tgggacagat ttcactctca ccatcagcag cctgcagcct      240
gaagattttg caacttatta ctgcttgcag tatgatgagt ttcctctcac atttggagga      300
gggaccaagg tggagatcaa a                                                321
```

<210> SEQ ID NO 38
<211> LENGTH: 321
<212> TYPE: DNA
<213> ORGANISM: Artificial Sequence
<220> FEATURE:
<223> OTHER INFORMATION: Synthesized

<400> SEQUENCE: 38

```
gacatccaga tgacccagtc tccatcctca ctgtctgcat ctgtaggaga cagagtcacc       60
atcaattgta aggctagtca ggacattaat agctatttga gctggtttca gcagaaacca      120
gggaaagccc ctaagaccct gatctataga gcaaatagat tggtagatgg ggtcccatca      180
aggttctctg gcagtggatc tgggcaagat tatactctca ccatcagcag cctgcagcct      240
gaagattttg caacttatta ctgcttgcag tatgatgagt ttcctctcac atttggagga      300
gggaccaagg tggagatcaa a                                                321
```

<210> SEQ ID NO 39
<211> LENGTH: 351
<212> TYPE: DNA
<213> ORGANISM: Artificial Sequence
<220> FEATURE:
<223> OTHER INFORMATION: Synthesized

<400> SEQUENCE: 39

```
caggttcagc tggtgcagtc tggagctgag gtgaagaagc ctggggcctc agtgaaggtc       60
tcctgcaagg cttctggtta cacctttacc aattatgata taaattgggt gagacaggcc      120
cctggacaag gcttgagtg gatgggatgg atttatcctg agatggtag taccaaatat       180 aatgagaaat tcaaggccag agtcaccatg accacagaca catccaccag cacagcctac      240
atggagctga ggagcctgag atctgatgac acagctgtgt attactgtgc tagaggatat      300
gaagatgcta tggactactg ggggcaaggg accacagtca cagtctcctc a                351
```

<210> SEQ ID NO 40
<211> LENGTH: 351
<212> TYPE: DNA
<213> ORGANISM: Artificial Sequence
<220> FEATURE:
<223> OTHER INFORMATION: Synthesized

<400> SEQUENCE: 40

```
caggttcagc tggtgcagtc tggagctgag gtgaagaagc ctggggcctc agtgaaggtc       60
tcctgcaagg cttctggtta cacctttacc aattatgata taaattgggt gagacaggcc      120
cctggacaag gcttgagtg gatgggatgg atttatcctg agatggtag taccaaatat       180 aatgagaaat tcaaggccag agtcaccatg acagctgaca catccaccag cacagcctac      240
atggagctga ggagcctgag atctgatgac acagctgtgt attactgtgc tagaggatat      300
gaagatgcta tggactactg ggggcaaggg accacagtca cagtctcctc a                351
```

<210> SEQ ID NO 41
<211> LENGTH: 351
<212> TYPE: DNA

<213> ORGANISM: Artificial Sequence
<220> FEATURE:
<223> OTHER INFORMATION: Synthesized

<400> SEQUENCE: 41

| | | | | | |
|---|---|---|---|---|---|
| caggttcagc | tggtgcagtc | tggagctgag | gtgaagaagc | ctggggcctc | agtgaaggtc | 60 |
| tcctgcaagg | cttctggtta | cacctttacc | aattatgata | taaattgggt | gagacaggcc | 120 |
| cctggacaag | ggcttgagtg | gatgggatgg | atttatcctg | gagatggtag | taccaaatat | 180 |
| aatgagaaat | tcaaggccag | agtcaccatg | accacagaca | catccaccag | cacagcctac | 240 |
| atggagctga | ggagcctgag | atctgatgac | acagctgtgt | attactgtgc | ttctggatat | 300 |
| gaagatgcta | tggactactg | ggggcaaggg | accacagtca | cagtctcctc | a | 351 |

<210> SEQ ID NO 42
<211> LENGTH: 351
<212> TYPE: DNA
<213> ORGANISM: Artificial Sequence
<220> FEATURE:
<223> OTHER INFORMATION: Synthesized

<400> SEQUENCE: 42

| | | | | | |
|---|---|---|---|---|---|
| caggttcagc | tggtgcagtc | tggagctgag | gtgaagaagc | ctggggcctc | agtgaaggtc | 60 |
| tcctgcaagg | cttctggtta | cacctttacc | aattatgata | taaattgggt | gagacaggcc | 120 |
| cctggacaag | ggcttgagtg | gatgggatgg | atttatcctg | gagatggtag | taccaaatat | 180 |
| aatgagaaat | tcaaggccag | agtcaccatg | accacagaca | agtccaccag | cacagcctac | 240 |
| atggagctga | ggagcctgag | atctgatgac | acagctgtgt | attactgtgc | tagaggatat | 300 |
| gaagatgcta | tggactactg | ggggcaaggg | accacagtca | cagtctcctc | a | 351 |

<210> SEQ ID NO 43
<211> LENGTH: 351
<212> TYPE: DNA
<213> ORGANISM: Artificial Sequence
<220> FEATURE:
<223> OTHER INFORMATION: Synthesized

<400> SEQUENCE: 43

| | | | | | |
|---|---|---|---|---|---|
| caggttcagc | tggtgcagtc | tggagctgag | gtgaagaagc | ctggggcctc | agtgaaggtc | 60 |
| tcctgcaagg | cttctggtta | cacctttacc | aattatgata | taaattgggt | gagacaggcc | 120 |
| cctggacaag | ggcttgagtg | gattggatgg | atttatcctg | gagatggtag | taccaaatat | 180 |
| aatgagaaat | tcaaggccag | agtcaccatg | accacagaca | catccaccag | cacagcctac | 240 |
| atggagctga | ggagcctgag | atctgatgac | acagctgtgt | attactgtgc | tagaggatat | 300 |
| gaagatgcta | tggactactg | ggggcaaggg | accacagtca | cagtctcctc | a | 351 |

<210> SEQ ID NO 44
<211> LENGTH: 351
<212> TYPE: DNA
<213> ORGANISM: Artificial Sequence
<220> FEATURE:
<223> OTHER INFORMATION: Synthesized

<400> SEQUENCE: 44

| | | | | | |
|---|---|---|---|---|---|
| caggttcagc | tggtgcagtc | tggagctgag | gtgaagaagc | ctggggcctc | agtgaaggtc | 60 |
| tcctgcaagg | cttctggtta | cacctttacc | aattatgata | taaattgggt | gaaccagagg | 120 |
| cctggacaag | ggcttgagtg | gatgggatgg | atttatcctg | gagatggtag | taccaaatat | 180 |
| aatgagaaat | tcaaggccag | agtcaccatg | accacagaca | catccaccag | cacagcctac | 240 |

```
atggagctga ggagcctgag atctgatgac acagctgtgt attactgtgc tagaggatat      300
gaagatgcta tggactactg ggggcaaggg accacagtca cagtctcctc a               351
```

<210> SEQ ID NO 45  
<211> LENGTH: 351  
<212> TYPE: DNA  
<213> ORGANISM: Artificial Sequence  
<220> FEATURE:  
<223> OTHER INFORMATION: Synthesized
<400> SEQUENCE: 45

```
caggttcagc tggtgcagtc tggagctgag gtgaagaagc ctggggcctc agtgaaggtc       60
tcctgcaagg cttctggtta ccctttacc aattatgata taaattgggt gagacaggcc       120
cctggacaag gcttgagtg gatgggatgg atttatcctg agatggtag taccaaatat       180 aatgagaaat tcaaggccaa ggctaccctg accacagaca catccaccag cacagcctac      240
atggagctga ggagcctgag atctgatgac acagctgtgt attactgtgc tagaggatat      300
gaagatgcta tggactactg ggggcaaggg accacagtca cagtctcctc a               351
```

<210> SEQ ID NO 46  
<211> LENGTH: 351  
<212> TYPE: DNA  
<213> ORGANISM: Artificial Sequence  
<220> FEATURE:  
<223> OTHER INFORMATION: Synthesized
<400> SEQUENCE: 46

```
caggttcagc tggtgcagtc tggagctgag gtgaagaagc ctggggcctc agtgaaggtc       60
tcctgcaagg cttctggtta caccttaccc aattatgata taaattgggt gagacaggcc      120
cctggacaag gcttgagtg gatgggatgg atttatcctg agatggtag taccaaatat       180 aatgagaaat tcaaggccag agtcaccatg accacagaca catccaccag cacagcctac      240
atggagctga gcagcctgac ctctgatgac acagctgtgt attactgtgc tagaggatat      300
gaagatgcta tggactactg ggggcaaggg accacagtca cagtctcctc a               351
```

<210> SEQ ID NO 47  
<211> LENGTH: 351  
<212> TYPE: DNA  
<213> ORGANISM: Artificial Sequence  
<220> FEATURE:  
<223> OTHER INFORMATION: Synthesized
<400> SEQUENCE: 47

```
caggttcagc tggtgcagtc tggagctgag gtgaagaagc ctggggcctc agtgaaggtc       60
tcctgcaagg cttctggtta cacctttacc aattatgata taaattgggt gagacaggcc      120
cctggacaag gcttgagtg gattggatgg atttatcctg agatggtag taccaaatat       180 aatgagaaat tcaaggccaa ggctaccctg acagctgaca catccaccag cacagcctac      240
atggagctga ggagcctgag atctgatgac acagctgtgt attactgtgc ttctggatat      300
gaagatgcta tggactactg ggggcaaggg accacagtca cagtctcctc a               351
```

<210> SEQ ID NO 48  
<211> LENGTH: 318  
<212> TYPE: DNA  
<213> ORGANISM: Homo sapiens
<400> SEQUENCE: 48

| | |
|---|---:|
| acggtggctg caccatctgt cttcatcttc cgccatctg atgagcagtt gaaatctgga | 60 |
| actgcctctg ttgtgtgcct gctgaataac ttctatccca gagaggccaa agtacagtgg | 120 |
| aaggtggata acgccctcca atcgggtaac tcccaggaga gtgtcacaga gcaggacagc | 180 |
| aaggacagca cctacagcct cagcagcacc ctgacgctga gcaaagcaga ctacgagaaa | 240 |
| cacaaagtct acgcctgcga agtcacccat cagggcctga gctcgcccgt cacaaagagc | 300 |
| ttcaacaggg gagagtgt | 318 |

<210> SEQ ID NO 49
<211> LENGTH: 990
<212> TYPE: DNA
<213> ORGANISM: Homo sapiens

<400> SEQUENCE: 49

| | |
|---|---:|
| gctagcacca agggcccatc tgtcttcccc ctggcaccct cctccaagag cacctctggg | 60 |
| ggcacagctg ccctgggctg cctggtcaag gactacttcc ctgaacctgt gacagtgtcc | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagaa agttgagccc | 300 |
| aaatcttgtg acaaaactca cacatgccca ccgtgcccag cacctgaact cctgggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcaaggtctc caacaaagcc ctcccagccc ccatcgagaa aaccatctcc | 660 |
| aaagccaaag ggcagccccg agaaccacag gtgtacaccc tgcccccatc ccgggatgag | 720 |
| ctgaccaaga accaggtcag cctgacctgc ctggtcaaag gcttctatcc cagcgacatc | 780 |
| gccgtggagt gggagagcaa tgggcagccg gagaacaact acaagaccac gcctcccgtg | 840 |
| ctggactccg acggctcctt cttcctctac agcaagctca ccgtggacaa gagcaggtgg | 900 |
| cagcagggga acgtcttctc atgctccgtg atgcatgagg ctctgcacaa ccactacaca | 960 |
| cagaagagcc tctccctgtc tccgggtaaa | 990 |

<210> SEQ ID NO 50
<211> LENGTH: 987
<212> TYPE: DNA
<213> ORGANISM: Homo sapiens

<400> SEQUENCE: 50

| | |
|---|---:|
| gctagcacca agggcccatc tgtcttcccc ctggcaccct cctccaagag cacctctggg | 60 |
| ggcacagctg ccctgggctg cctggtcaag gactacttcc ctgaacctgt gacagtgtcc | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagaa agttgagccc | 300 |
| aaatcttgtg acaaaactca cacatgccca ccgtgcccag cacctgaact cctgggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |

```
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacaca    960
cagaagagcc tctccctgtc tccgggt                                        987
```

<210> SEQ ID NO 51
<211> LENGTH: 990
<212> TYPE: DNA
<213> ORGANISM: Artificial Sequence
<220> FEATURE:
<223> OTHER INFORMATION: Synthesized

<400> SEQUENCE: 51

```
gctagcacca agggcccatc tgtcttcccc ctggcaccct cctccaagag cacctctggg     60
ggcacagctg ccctgggctg cctggtcaag gactacttcc ctgaacctgt gacagtgtcc    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggggga    360 ccgtgtgtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacaca    960
cagaagagcc tctccctgtc tccgggtaaa                                     990
```

<210> SEQ ID NO 52
<211> LENGTH: 987
<212> TYPE: DNA
<213> ORGANISM: Artificial Sequence
<220> FEATURE:
<223> OTHER INFORMATION: Synthesized

<400> SEQUENCE: 52

```
gctagcacca agggcccatc tgtcttcccc ctggcaccct cctccaagag cacctctggg     60
ggcacagctg ccctgggctg cctggtcaag gactacttcc ctgaacctgt gacagtgtcc    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
```

```
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtgtgtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc catcgagaaa accatctcc    660 aaagccaaag gcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacaca    960
cagaagagcc tctccctgtc tccgggt                                       987
```

<210> SEQ ID NO 53
<211> LENGTH: 66
<212> TYPE: DNA
<213> ORGANISM: Artificial Sequence
<220> FEATURE:
<223> OTHER INFORMATION: Synthesized

<400> SEQUENCE: 53

```
atggacatga ggacccctgc tcagtttctt ggaatcttgt tgctctggtt tccaggtatc    60
aaatgt                                                              66
```

<210> SEQ ID NO 54
<211> LENGTH: 57
<212> TYPE: DNA
<213> ORGANISM: Artificial Sequence
<220> FEATURE:
<223> OTHER INFORMATION: Synthesized

<400> SEQUENCE: 54

```
atgggatgga gatggatctt tcttttcctc ctgtcgggaa ctgcaggtgt ccattgc       57
```

<210> SEQ ID NO 55
<211> LENGTH: 364
<212> TYPE: PRT
<213> ORGANISM: Homo sapiens

<400> SEQUENCE: 55

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp

```
            100                 105                 110
Asn Gly Ser Tyr Phe Arg Met Glu Arg Gly Ser Thr Lys Tyr Ser
            115                 120                 125

Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 56
<211> LENGTH: 359
<212> TYPE: PRT
<213> ORGANISM: Macaca fascicularis

<400> SEQUENCE: 56

Met Pro Leu Leu Leu Pro Leu Leu Trp Ala Gly Ala Leu Ala Met
1               5                   10                  15

Asp Pro Arg Val Arg Leu Glu Val Gln Glu Ser Val Thr Val Gln Glu
            20                  25                  30

Gly Leu Cys Val Leu Val Pro Cys Thr Phe Phe His Pro Val Pro Tyr
        35                  40                  45

His Thr Arg Asn Ser Pro Val His Gly Tyr Trp Phe Arg Glu Gly Ala
    50                  55                  60

Ile Val Ser Leu Asp Ser Pro Val Ala Thr Asn Lys Leu Asp Gln Glu
65                  70                  75                  80

Val Gln Glu Glu Thr Gln Gly Arg Phe Arg Leu Leu Gly Asp Pro Ser
                85                  90                  95

Arg Asn Asn Cys Ser Leu Ser Ile Val Asp Ala Arg Arg Arg Asp Asn
            100                 105                 110
```

```
Gly Ser Tyr Phe Phe Arg Met Glu Lys Gly Ser Thr Lys Tyr Ser Tyr
            115                 120                 125

Lys Ser Thr Gln Leu Ser Val His Val Thr Asp Leu Thr His Arg Pro
        130                 135                 140

Gln Ile Leu Ile Pro Gly Ala Leu Asp Pro Asp His Ser Lys Asn Leu
145                 150                 155                 160

Thr Cys Ser Val Pro Trp Ala Cys Glu Gln Gly Thr Pro Pro Ile Phe
                165                 170                 175

Ser Trp Met Ser Ala Ala Pro Thr Ser Leu Gly Leu Arg Thr Thr His
            180                 185                 190

Ser Ser Val Leu Ile Ile Thr Pro Arg Pro Gln Asp His Gly Thr Asn
        195                 200                 205

Leu Thr Cys Gln Val Lys Phe Pro Gly Ala Gly Val Thr Thr Glu Arg
210                 215                 220

Thr Ile Gln Leu Asn Val Ser Tyr Ala Ser Gln Asn Pro Arg Thr Asp
225                 230                 235                 240

Ile Phe Leu Gly Asp Gly Ser Gly Lys Gln Gly Val Val Gln Gly Ala
                245                 250                 255

Ile Gly Gly Ala Gly Val Thr Val Leu Leu Ala Leu Cys Leu Cys Leu
            260                 265                 270

Ile Phe Phe Thr Val Lys Thr His Arg Arg Lys Ala Ala Arg Thr Ala
        275                 280                 285

Val Gly Arg Ile Asp Thr His Pro Ala Thr Gly Pro Thr Ser Ser Lys
        290                 295                 300

His Gln Lys Lys Ser Lys Leu His Gly Ala Thr Glu Thr Ser Gly Cys
305                 310                 315                 320

Ser Gly Thr Thr Leu Thr Val Glu Met Asp Glu Glu Leu His Tyr Ala
                325                 330                 335

Ser Leu Asn Phe His Gly Met Asn Pro Ser Glu Asp Thr Ser Thr Glu
            340                 345                 350

Tyr Ser Glu Val Arg Thr Gln
        355

<210> SEQ ID NO 57
<211> LENGTH: 359
<212> TYPE: PRT
<213> ORGANISM: Macaca fascicularis

<400> SEQUENCE: 57

Met Pro Leu Leu Leu Leu Pro Leu Leu Trp Ala Gly Ala Leu Ala Met
1               5                   10                  15

Asp Pro Arg Val Arg Leu Glu Val Gln Glu Ser Val Thr Val Gln Glu
            20                  25                  30

Gly Leu Cys Val Leu Val Pro Cys Thr Phe Phe His Pro Val Pro Tyr
        35                  40                  45

His Ala Arg Asn Ser Pro Val His Gly Tyr Trp Phe Arg Glu Gly Ala
    50                  55                  60

Ile Val Ser Leu Asp Ser Pro Val Ala Thr Asn Lys Leu Asp Gln Glu
65                  70                  75                  80

Val Arg Glu Glu Thr Gln Gly Arg Phe Arg Leu Leu Gly Asp Pro Ser
                85                  90                  95

Arg Asn Asn Cys Ser Leu Ser Ile Val Asp Ala Arg Arg Arg Asp Asn
            100                 105                 110

Gly Ser Tyr Phe Phe Arg Met Glu Lys Gly Ser Thr Lys Tyr Ser Tyr
        115                 120                 125
```

```
Lys Ser Thr Gln Leu Ser Val His Val Thr Asp Leu Thr His Arg Pro
    130                 135             140
Gln Ile Leu Ile Pro Gly Ala Leu Asp Pro Asp His Ser Lys Asn Leu
145                 150                 155                 160
Thr Cys Ser Val Pro Trp Ala Cys Glu Gln Gly Thr Pro Pro Ile Phe
                165                 170                 175
Ser Trp Met Ser Ala Ala Pro Thr Ser Leu Gly Leu Arg Thr Thr His
            180                 185                 190
Ser Ser Val Leu Ile Ile Thr Pro Arg Pro Gln Asp His Gly Thr Asn
        195                 200                 205
Leu Thr Cys Gln Val Lys Phe Pro Gly Ala Gly Val Thr Thr Glu Arg
    210                 215                 220
Thr Ile Gln Leu Asn Val Ser Tyr Ala Ser Gln Asn Pro Arg Thr Asp
225                 230                 235                 240
Ile Phe Leu Gly Asp Gly Ser Gly Lys Gln Gly Val Val Gln Gly Ala
                245                 250                 255
Ile Gly Gly Ala Gly Val Thr Val Leu Leu Ala Leu Cys Leu Cys Leu
            260                 265                 270
Ile Phe Phe Thr Val Lys Thr His Arg Arg Lys Ala Ala Arg Thr Ala
            275                 280                 285
Val Gly Arg Ile Asp Thr His Pro Ala Thr Gly Pro Thr Ser Ser Lys
    290                 295                 300
His Gln Lys Lys Ser Lys Leu His Gly Ala Thr Glu Thr Ser Gly Cys
305                 310                 315                 320
Ser Gly Thr Thr Leu Thr Val Glu Met Asp Glu Glu Leu His Tyr Ala
                325                 330                 335
Ser Leu Asn Phe His Gly Met Asn Pro Ser Glu Asp Thr Ser Thr Glu
            340                 345                 350
Tyr Ser Glu Val Arg Thr Gln
            355
```